US009427381B2

(12) United States Patent
Ishihara et al.

(10) Patent No.: US 9,427,381 B2
(45) Date of Patent: Aug. 30, 2016

(54) DENTAL CURABLE COMPOSITION, AND METHOD FOR PRODUCING SAME

(71) Applicant: KURARAY NORITAKE DENTAL INC., Kurashiki-shi (JP)

(72) Inventors: Shumei Ishihara, Tainai (JP); Kenji Hatanaka, Tainai (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 14/431,939

(22) PCT Filed: Sep. 26, 2013

(86) PCT No.: PCT/JP2013/075974
§ 371 (c)(1),
(2) Date: Mar. 27, 2015

(87) PCT Pub. No.: WO2014/050924
PCT Pub. Date: Apr. 3, 2014

(65) Prior Publication Data
US 2015/0202123 A1    Jul. 23, 2015

(30) Foreign Application Priority Data

Sep. 28, 2012  (JP) ................................. 2012-217244

(51) Int. Cl.
| A61K 6/00 | (2006.01) |
| A61K 6/027 | (2006.01) |
| A61K 6/033 | (2006.01) |
| A61K 6/06 | (2006.01) |
| A61K 6/083 | (2006.01) |

(52) U.S. Cl.
CPC ........... *A61K 6/0082* (2013.01); *A61K 6/0088* (2013.01)

(58) Field of Classification Search
None
See application file for complete search history.

(56) References Cited

U.S. PATENT DOCUMENTS

| 4,089,830 A * | 5/1978 | Tezuka ................. A61K 6/0835 106/35 |
| 4,518,430 A | 5/1985 | Brown et al. |
| 5,776,233 A | 7/1998 | Wiedemann et al. |
| 2002/0039957 A1 * | 4/2002 | Kobayashi ........... A61K 6/0835 501/20 |
| 2003/0087986 A1 | 5/2003 | Mitra |
| 2013/0189337 A1 * | 7/2013 | Hashimoto .......... A61K 6/0017 424/401 |
| 2015/0202123 A1 * | 7/2015 | Ishihara ............... A61K 6/0088 523/116 |

FOREIGN PATENT DOCUMENTS

| JP | 2 250810 | 10/1990 |
| JP | 8 239250 | 9/1996 |
| JP | 2001 354509 | 12/2001 |
| JP | 2002 60342 | 2/2002 |
| JP | WO 2012046667 A1 * | 4/2012 ........... A61K 6/0017 |

OTHER PUBLICATIONS

Hong, et al., "The Effect of Nano-Sized β-Tricalcium Phosphate on Remineralization in Glass Ionomer Dental Luting Cement", Key Engineering Materials, vol. 361-363, (2008), pp. 861-864.
Tenhuisen, et al., "The Formation of Hydroxyapatite-Ionomer Cements at 38 ° C.", Journal of Dental Research, vol. 73, No. 3, (Mar. 1994), pp. 598-606.
Ten Cate, et al., "Hypermineralization of Dentinal Lesions Adjacent to Glass-ionomer Cement Restorations", Journal of Dental Research, vol. 74, No. 6, (Jun. 1995), pp. 1266-1271.
International Search Report Issued Jan. 7, 2014 in PCT/JP13/075974 Filed Sep. 26, 2013.
Extended Search Report issued Mar. 18, 2016, in European patent application No. 13840214.4.

* cited by examiner

*Primary Examiner* — Peter A Salamon
(74) *Attorney, Agent, or Firm* — Oblon, McClelland, Maier & Neustadt, L.L.P.

(57) ABSTRACT

A dental curable composition containing fluoroaluminosilicate glass particles (A), basic calcium phosphate particles (B1), acidic calcium phosphate particles (B2), a polyalkenic acid (C), tartaric acid (D), and water (E), wherein the dental curable composition contains 70 to 99 parts by weight of (A), 1 to 30 parts by weight in total of (B1) and (B2), 10 to 40 parts by weight of (C), 0.3 to 10 parts by weight of (D), and 10 to 90 parts by weight of (E) each relative to 100 parts by weight in total of (A), (B1), and (B2), and a Ca/P ratio of a sum of (B1) and (B2) is from 1.10 to 1.95. Accordingly, provided is a dental curable composition that is high in mechanical strength, particularly compressive strength, and excellent in remineralization capability.

20 Claims, No Drawings

DENTAL CURABLE COMPOSITION, AND METHOD FOR PRODUCING SAME

TECHNICAL FIELD

The present invention relates to a dental curable composition which is effective in improving the physical properties of a cured product and remineralization capability to tooth substance as compared with conventional glass ionomer cements.

BACKGROUND ART

Glass ionomer cements are used by making a polymer acid primarily containing an acid such as a polycarboxylic acid and a glass powder for a glass ionomer cement react together to be cured in the presence of water. Glass ionomer cements have characteristics such that they are good in affinity to a living body, that they have superior adhesion to tooth substance such as enamel or dentin, and that they have tooth substance remineralization action and anti-caries action owing to fluorine contained in a glass powder. For these reasons, glass ionomer cements are materials widely used in dentistry for filling of a caries cavity, attachment of a crown, an inlay, a bridge or an orthodontic band, lining of a cavity, a sealer for filling a root canal, core construction, prophylactic sealing, and the like.

However, glass ionomer cements are low in mechanical strength such as compressive strength as compared with resin-based cements and the like including resin as a main component. When a stress is applied, the glass ionomer cements have a drawback that they are readily broken due to fine voids or defects in the interior of a cement cured product, cracks from scratches on a surface of the cured product, and the like. This is considered to be as follows: a matrix portion constituted by allowing a polycarboxylic acid, water, and a glass powder surface portion to react is brittle as compared with a glass portion constituted via a firm covalent bond of Si—O or Al—O and having a homogenous three-dimensional network structure, so that when a stress is concentrated into fine cracks generated in a part of the cured product, the cracks evade the glass portion having high strength and are rapidly expanded in the matrix portion having low strength, whereby the cured product is broken. As a result, in the dentistry, glass ionomer cements cannot be applied for filling a cavity to which a relatively large load is added, such as a class II cavity or a class IV cavity, and it has been reported that they are insufficient in mechanical strengths as compared with resin-based cements.

Along with a so-called "8020 campaign" (improvement in dental health, preservation of tooth substance (MI: Minimal Intervention)) to try to keep 20 or more own teeth even when being 80 years old, a remineralization therapy in which a site affected by caries is prevented from grinding as much as possible and a remaining site affected by caries is returned to the original with a material has recently got into the spotlight. A glass ionomer cement has been widely recognized also as a restorative material that slowly releases fluorine ions, which are known as an effective component for remineralization, and can possibly reduce the grinding amount of tooth substance. However, hydroxyapatite serving as a main constituent of tooth substance such as enamel or dentin is a compound comprising calcium or phosphorus, and efficient remineralization of a site affected by caries is not promoted sufficiently by supplying only fluorine ions to tooth substance.

Patent Document 1 discloses a glass ionomer cement powder containing apatite that fully makes use of biocompatibility and adhesion to tooth substance, both the biocompatibility and the adhesion to tooth substance being characteristics of a conventional glass ionomer cement, and is capable of increasing mechanical strength. It has been reported that mechanical strength, particularly three-points bending strength and tensile strength, increases as compared with the case where a conventional glass powder for a dental glass ionomer cement is used and that a glass ionomer cement can also be applied for filling a cavity to which a large load is to be added, the filling having been believed to be insufficient in conventional dentistry. Although the mechanical strength of a glass ionomer cement can increase, there is a problem that calcium or phosphorus, which is main constituents of tooth substance, cannot be supplied sufficiently to demineralized tooth substance, and efficient remineralization cannot be promoted by merely adding hydroxyapatite, which is believed to be most stable among calcium phosphates.

Non-Patent Document 1 discloses that when amalgam, a composite resin, and a glass ionomer cement having sustained fluorine releasability are filled into dentin cavities with remaining caries-like tissue, and then the degree of remineralization in each sample is evaluated after a lapse of 12 weeks with microradiography, and as a result, demineralization advanced in the caries-like tissues located near the cavities into which amalgam and the composite resin are filled, respectively, whereas remineralization is observed in the caries-like tissue near the cavity into which the glass ionomer cement is filled. Accordingly, it has been reported that a glass ionomer cement is an effective material for realizing preservation of tooth substance (MI: Minimal Intervention). As described above, however, a glass ionomer cement merely having sustained fluorine releasability cannot realize efficient remineralization, and a problem regarding low mechanical strength still remains unsolved.

As described in the prior art documents, the conventional technologies have a drawback that low mechanical strength and insufficient remineralization capability possessed by a glass ionomer cement cannot be solved, and solution of these problems have been desired.

PRIOR ART DOCUMENTS

Patent Document
Patent Document 1: JP 2001-354509 A
Non-Patent Document
Non-Patent Document 1: Ten Cate J M et al., Hypermineralization of dentinal lesions adjacent to glass-ionomer cement restorations. J Dent Res. 1995 June; 74(6): 1266-71.

SUMMARY OF THE INVENTION

Problems to be Solved by the Invention

The present invention was devised in order to solve the above-described problems, and an object thereof is to provide a dental curable composition that is high in mechanical strength, particularly compressive strength, and excellent in remineralization capability.

Means for Solving the Problems

The above-mentioned problems can be solved by providing a dental curable composition comprising:

fluoroaluminosilicate glass particles (A), basic calcium phosphate particles (B1), acidic calcium phosphate particles (B2), a polyalkenic acid (C), tartaric acid (D), and water (E), wherein the dental curable composition comprises 70 to 99 parts by weight of the fluoroaluminosilicate glass particles (A), 1 to 30 parts by weight in total of the basic calcium phosphate particles (B1) and the acidic calcium phosphate particles (B2), 10 to 40 parts by weight of the polyalkenic acid (C), 0.3 to 10 parts by weight of the tartaric acid (D), and 10 to 90 parts by weight of the water (E) each relative to 100 parts by weight in total of the fluoroaluminosilicate glass particles (A), the basic calcium phosphate particles (B1), and the acidic calcium phosphate particles (B2), and a Ca/P ratio of a sum of the basic calcium phosphate particles (B1) and the acidic calcium phosphate particles (B2) is from 1.10 to 1.95.

At this time, the basic calcium phosphate particles (B1) are preferably at least one member selected from the group consisting of particles of tetracalcium phosphate [$Ca_4(PO_4)_2O$] and particles of octacalcium phosphate pentahydrate [$Ca_8H_2(PO_4)_6 \cdot 5H_2O$], and the acidic calcium phosphate particles (B2) are at least one member selected from the group consisting of particles of anhydrous calcium monohydrogen phosphate [$CaHPO_4$], particles of tricalcium phosphate [$Ca_3(PO_4)_2$], particles of anhydrous calcium dihydrogen phosphate [$Ca(H_2PO_4)_2$], particles of amorphous calcium phosphate [$Ca_3(PO_4)_2 \cdot xH_2O$], particles of acidic calcium pyrophosphate [$CaH_2P_2O_7$], particles of calcium monohydrogen phosphate dihydrate [$CaHPO_4 \cdot 2H_2O$], and particles of calcium dihydrogen phosphate monohydrate [$Ca(H_2PO_4)_2 \cdot H_2O$]. And the dental curable composition is preferably a glass ionomer cement.

The above-mentioned problems can be solved by providing a method for producing a dental curable composition, the method comprising mixing a powder agent (X) comprising at least fluoroaluminosilicate glass particles (A), basic calcium phosphate particles (B1), and acidic calcium phosphate particles (B2), with a liquid agent (Y) comprising at least a polyalkenic acid (C), tartaric acid (D), and water (E), wherein a weight ratio (X/Y) of the powder agent (X) to the liquid agent (Y) is from 1.0 to 5.0. At this time, preferably, the fluoroaluminosilicate glass particles (A) have an average particle size of from 0.3 to 35 μm, the basic calcium phosphate particles (B1) have an average particle size of from 3 to 35 μm, and the acidic calcium phosphate particles (B2) have an average particle size of from 0.3 to 10 μm.

Moreover, the above-mentioned problems can also be solved by providing a dental curable composition kit comprising: a powder agent (X) comprising at least fluoroaluminosilicate glass particles (A), basic calcium phosphate particles (B1), and acidic calcium phosphate particles (B2), and a liquid agent (Y) comprising at least a polyalkenic acid (C), tartaric acid (D), and water (E), wherein the powder agent (X) and the liquid agent (Y) are mixed in a weight ratio (X/Y) within a range of from 1.0 to 5.0. At this time, preferably, the fluoroaluminosilicate glass particles (A) have an average particle size of from 0.3 to 35 μm, the basic calcium phosphate particles (B1) have an average particle size of from 3 to 35 μm, and the acidic calcium phosphate particles (B2) have an average particle size of from 0.3 to 10 μm.

Effects of the Invention

According to the present invention, there is provided a dental curable composition that is high in mechanical strength, particularly compressive strength, and excellent in remineralization capability. Thus, the dental curable composition cannot only be applied for filling a cavity to which a relatively large load is to be added, but also allows for a remineralization treatment in which a site affected by caries is prevented from grinding as much as possible and a remaining site affected by caries is returned to the original with a material.

MODES FOR CARRYING OUT THE INVENTION

The dental curable composition of the present invention is a dental curable composition comprising:
fluoroaluminosilicate glass particles (A), basic calcium phosphate particles (B1), acidic calcium phosphate particles (B2), a polyalkenic acid (C), tartaric acid (D), and water (E), wherein the dental curable composition comprises 70 to 99 parts by weight of the fluoroaluminosilicate glass particles (A), 1 to 30 parts by weight in total of the basic calcium phosphate particles (B1) and the acidic calcium phosphate particles (B2), 10 to 40 parts by weight of the polyalkenic acid (C), 0.3 to 10 parts by weight of the tartaric acid (D), and 10 to 90 parts by weight of the water (E) each relative to 100 parts by weight in total of the fluoroaluminosilicate glass particles (A), the basic calcium phosphate particles (B1), and the acidic calcium phosphate particles (B2), and a Ca/P ratio of a sum of the basic calcium phosphate particles (B1) and the acidic calcium phosphate particles (B2) is from 1.10 to 1.95. The dental curable composition of the present invention makes it possible to increase mechanical strength, particularly compressive strength with time, and promote remineralization of tooth substance. Although its action mechanism is not necessarily clear, the following mechanism is presumed.

That is, it is presumed that the above-mentioned effect is attained by adding certain amounts of basic calcium phosphate particles (B1) and acidic calcium phosphate particles (B2), which are starting materials for calcium phosphate cement that forms thermodynamically stable hydroxyapatite to be cured via a hydration reaction upon kneading in the presence of water, to fluoroaluminosilicate glass particles (A), a polyalkenic acid (C), and water (E), which are starting materials for glass ionomer cement that is cured via an acid-base reaction (glass ionomer reaction). The use of the configuration of the present invention is worthy in the following two aspects, i.e., that a hydration and curing reaction of two types of calcium phosphate particles (B1) and (B2) with water is slower than a glass ionomer reaction in which a polyalkenic acid having an anion (carboxyl group, $-COO^-$) forms a network structure to be cured via a cation (aluminum ion or the like) dissociated from fluoroaluminosilicate glass, and that calcium ions or phosphate ions are released in a hydration reaction between calcium phosphate particles and water. In other words, effective remineralization of tooth substance may be possible because compressive strength increases with time through the hydration reaction between calcium phosphate particles and water that is presumed to occur subsequently to the glass ionomer reaction, and moreover, release of ions of calcium or phosphorus, which are major constituent elements of tooth substance, can be provided in addition to sustained fluorine releasability possessed inherently by a glass ionomer cement.

The dental curable composition of the present invention is required to contain 70 to 99 parts by weight of the fluoroaluminosilicate glass particles (A) relative to 100 parts by weight in total of the fluoroaluminosilicate glass particles (A), the basic calcium phosphate particles (B1), and the acidic calcium phosphate particles (B2). When the content of the fluoroaluminosilicate glass particles (A) is less than 70 parts by weight, sufficient mechanical strength may not be attained because a three-dimensional network structure resulting from a glass ionomer reaction cannot be formed sufficiently. Accordingly, the content is preferably 80 parts by weight or more, more preferably 90 parts by weight or more. On the other hand, when the content of the fluoroaluminosilicate glass particles (A) exceeds 99 parts by weight, an increase in compressive strength with time and remineralization capability of tooth substance may not be sufficiently developed because a hydration reaction caused by calcium phosphate particles may be inhibited and even sufficient release of calcium ions and phosphate ions may not be attained. Accordingly, the content is preferably 98 parts by weight or less, more preferably 97 parts by weight or less.

The fluoroaluminosilicate glass particles (A) to be used for the present invention preferably have an average particle size of from 0.3 to 35 µm. When the fluoroaluminosilicate glass particles (A) have an average particle size of smaller than 0.3 µm, the average particle size is so small that the particles are difficult to be produced and the viscosity of a paste resulting from mixing with a liquid agent may become excessively high. The fluoroaluminosilicate glass particles (A) have an average particle size of more preferably 0.5 µm or more, particularly preferably 1 µm or more. On the other hand, when the fluoroaluminosilicate glass particles (A) have an average particle size of larger than 35 µm, the paste resulting from mixing with a liquid agent may have undesirable paste properties, for example, the paste fails to exhibit sufficient viscosity. Moreover, operability may be impaired due to an increase in sandy feeling at the time of kneading the paste, and furthermore unpleasant impression may be given to the tongue of a patient when the paste is applied in the oral cavity. The fluoroaluminosilicate glass particles (A) have an average particle size of more preferably 30 µm or less, particularly preferably 10 µm or less. Herein, the average particle size of the fluoroaluminosilicate glass particles (A) to be used for the present invention is a value measured with a laser diffraction particle size distribution analyzer to be calculated.

The method for producing the fluoroaluminosilicate glass particles (A) to be used for the present invention is not particularly restricted. A commercially available fluoroaluminosilicate glass powder may be used as it is, or alternatively a commercial product may be further pulverized. In this case, a pulverizing apparatus such as a ball mill, a pestle and mortar machine, or a jet mill may be used. Moreover, known fluoroaluminosilicate glass particles may be used which have heretofore been used as a powder component of a dental glass ionomer cement. For example, a fine powder can be prepared by weighing a glass raw material selected from silica stone, alumina, aluminum hydroxide, aluminum silicate, mullite, calcium silicate, strontium silicate, sodium silicate, aluminum carbonate, calcium carbonate, strontium carbonate, sodium carbonate, sodium fluoride, calcium fluoride, aluminum fluoride, strontium fluoride, aluminum phosphate, calcium phosphate, strontium phosphate, sodium phosphate, etc., melting the raw material at a temperature equal to or higher than 1000° C., and then cooling the resulting product, followed by pulverization. In this case, a pulverizing apparatus such as a ball mill, a pestle and mortar machine, or a jet mill may be used. After cooling, a glass powder with desired average particle size and desired particle size distribution can be obtained by powdering the resulting glass material (frit) with pulverizing means such as a ball mill, and as necessary, performing classification treatment such as sieving. Moreover, the fluoroaluminosilicate glass particles (A) can also be obtained by pulverizing a fluoroaluminosilicate glass raw material powder together with a liquid medium such as alcohol, with the use of a pestle and mortar machine, a ball mill, or the like to prepare a slurry, and then drying the resulting slurry. At this time, a ball mill is preferably used as a pulverizing apparatus, and alumina or zirconia is preferably used as the material for the pot and balls of the ball mill.

The dental curable composition of the present invention is required to contain 1 to 30 parts by weight in total of the basic calcium phosphate particles (B1) and the acidic calcium phosphate particles (B2) relative to 100 parts by weight in total of the fluoroaluminosilicate glass particles (A), the basic calcium phosphate particles (B1), and the acidic calcium phosphate particles (B2). When the content of the basic calcium phosphate particles (B1) and the acidic calcium phosphate particles (B2) in total is less than 1 part by weight, there may be no prospect of increase in compressive strength with time due to failure of a hydration reaction among the basic calcium phosphate particles (B1), the acidic calcium phosphate particles (B2), and water, and the discharged amount of calcium ions or phosphate ions for developing sufficient remineralization may not be much enough. The content of the basic calcium phosphate particles (B1) and the acidic calcium phosphate particles (B2) in total is preferably 2 parts by weight or more, particularly preferably 3 parts by weight or more. On the other hand, when the content of the basic calcium phosphate particles (B1) and the acidic calcium phosphate particles (B2) in total exceeds 30 parts by weight, it may not be possible to secure moderate operability because the reaction between the polyalkenic acid (C) and the basic calcium phosphate particles (B1) is faster than the reaction between the polyalkenic acid (C) and the fluoroaluminosilicate glass particles (A). Moreover, sufficient mechanical strength may not be obtained because the formation of a three-dimensional network structure via a glass ionomer reaction derived from the fluoroaluminosilicate glass particles (A) is inhibited. The content of the basic calcium phosphate particles (B1) and the acidic calcium phosphate particles (B2) in total is preferably 20 parts by weight or less, particularly preferably 10 parts by weight or less.

The basic calcium phosphate particles (B1) to be used for the present invention are not particularly restricted, and are preferably at least one member selected from the group consisting of particles of tetracalcium phosphate [$Ca_4(PO_4)_2O$] and particles of octacalcium phosphate pentahydrate [$Ca_8H_2(PO_4)_6 \cdot 5H_2O$]. Among these, particles of tetracalcium phosphate [$Ca_4(PO_4)_2O$] are particularly preferably used from the viewpoint of remineralization capability.

The basic calcium phosphate particles (B1) to be used for the present invention preferably have an average particle size of 3 to 35 µm. When the average particle size is less than 3 µm, the remineralization effect may not be attained as a result of failure in smooth precipitation of hydroxyapatite due to an increase in the pH of an aqueous solution caused by excessive dissolution of the basic calcium phosphate particles (B1). The basic calcium phosphate particles (B1) have an average particle size of more preferably 5 µm or more, particularly preferably 15 µm or more. On the other hand, when the average particle size exceeds 35 µm, a paste resulting from mixing with a liquid agent may have undesirable properties, for example, the paste fails to exhibit sufficient viscosity. Moreover, the particles (B1) are difficult to be soluble in water (E) to lose a supply balance between calcium ions and phosphate ions, so that the remineralization effect may deteriorate. Furthermore, operability may be impaired due to an increase in sandy feeling at the time of kneading the paste. The basic calcium phosphate particles (B1) have an average particle size of more preferably 30 μm or less, particularly preferably 25 μm or less. Herein, the average particle size of the basic calcium phosphate particles (B1) to be used for the present invention is calculated in the same manner as for the average particle size of the above-described fluoroaluminosilicate glass particles (A).

The method for producing the basic calcium phosphate particles (B1) to be used for the present invention is not particularly restricted. Commercially available basic calcium phosphate particles may be used as they are, or alternatively they may be used after regulating their particle size by appropriate pulverization. As a pulverization method, there can be used a method which is the same as the method for pulverizing the acidic calcium phosphate particles (B2) described below.

While the acidic calcium phosphate particles (B2) to be used for the present invention are not particularly restricted, they are preferably at least one member selected from the group consisting of particles of anhydrous calcium monohydrogen phosphate [CaHPO$_4$], particles of tricalcium phosphate [Ca$_3$(PO$_4$)$_2$], particles of anhydrous calcium dihydrogen phosphate [Ca(H$_2$PO$_4$)$_2$], particles of amorphous calcium phosphate [Ca$_3$(PO$_4$)$_2$.xH$_2$O], particles of acidic calcium pyrophosphate [CaH$_2$P$_2$O$_7$], particles of calcium monohydrogen phosphate dihydrate [CaHPO$_4$.2H$_2$O], and particles of calcium dihydrogen phosphate monohydrate [Ca(H$_2$PO$_4$)$_2$*H$_2$O]. Among these, at least one member selected from the group consisting of particles of anhydrous calcium monohydrogen phosphate [CaHPO$_4$], particles of tricalcium phosphate [Ca$_3$(PO$_4$)$_2$], particles of anhydrous calcium dihydrogen phosphate [Ca(H$_2$PO$_4$)$_2$], and particles of calcium monohydrogen phosphate dihydrate [CaHPO$_4$.2H$_2$O] are preferably used, at least one member selected from the group consisting of particles of anhydrous calcium monohydrogen phosphate [CaHPO$_4$] and particles of calcium monohydrogen phosphate dihydrate [CaHPO$_4$.2H$_2$O] are more preferably used, and from the viewpoint of remineralization capability, particles of anhydrous calcium monohydrogen phosphate [CaHPO$_4$] are particularly preferably used.

The acidic calcium phosphate particles (B2) to be used for the present invention preferably have an average particle size of 0.3 to 10 μm. When the average particle size is less than 0.3 μm, not only a supply balance between calcium ions and phosphate ions may be lost due to excessive dissolution of the acidic calcium phosphate particles (B2) in a liquid agent, but also the viscosity of a paste resulting from mixing with a liquid agent may be excessively high. Accordingly, the average particle size is more preferably 0.4 μm or more, particularly preferably 0.5 μm or more. On the other hand, when the average particle size exceeds 10 μm, the acidic calcium phosphate particles (B2) may be difficult to be soluble in water (E). As a result, a supply balance between calcium ions and phosphate ions may be lost, so that the remineralization effect may deteriorate. The acidic calcium phosphate particles (B2) have an average particle size of more preferably 5 μm or less, particularly preferably 3 μm or less. The average particle size of the acidic calcium phosphate particles (B2) is calculated in the same manner as for the average particle size of the fluoroaluminosilicate glass particles (A).

The method for producing the acidic calcium phosphate particles (B2) having such an average particle size is not particularly restricted. A commercial product may be used, if available, but a commercial product is preferably further pulverized in many cases. In this case, a pulverizing apparatus such as a ball mill, a pestle and mortar machine, or a jet mill may be used. Moreover, the acidic calcium phosphate particles (B2) can also be obtained by pulverizing an acidic calcium phosphate raw material powder together with a liquid medium such as alcohol, with the use of a pestle and mortar machine, a ball mill, or the like to prepare a slurry, and then drying the resulting slurry. At this time, a ball mill is preferably used as a pulverizing apparatus, and alumina or zirconia is preferably used as the material for the pot and balls of the ball mill.

By adjusting the average particle size of the basic calcium phosphate particles (B1) to be large than the average particle size of the acidic calcium phosphate particles (B2), the balance between the solubilities of both of the materials is made appropriate, so that it becomes possible to keep the pH in the composition to be almost neutral. As a result, precipitation of hydroxyapatite proceeds smoothly, and the remineralization effect is improved. Specifically, it is more preferable to adjust the average particle size of the basic calcium phosphate particles (B1) to twice or more, even more preferably four times or more, particularly preferably seven times or more the average particle size of the acidic calcium phosphate particles (B2). On the other hand, it is more preferable to adjust the average particle size of the basic calcium phosphate particles (B1) to 35 times or less, even more preferably 30 times or less, particularly preferably 25 times or less the average particle size of the acidic calcium phosphate particles (B2). While the blending ratio of the basic calcium phosphate particles (B1) to the acidic calcium phosphate particles (B2) is not particularly restricted, it is preferable, from the viewpoint of promotion of remineralization due to hydroxyapatite precipitation, to use both of the materials in a Ca/P ratio of the sum of the basic calcium phosphate particles (B1) and the acidic calcium phosphate particles (B2) of from 1.10 to 1.95, more preferably from 1.30 to 1.80, particularly preferably from 1.50 to 1.70. This makes it possible to obtain the dental curable composition of the present invention with an enhanced remineralization effect. The blending ratio (B1/B2) of the basic calcium phosphate particles (B1) to the acidic calcium phosphate particles (B2) is from 40/60 to 60/40 in molar ratio.

The dental curable composition of the present invention is required to contain 10 to 40 parts by weight of the polyalkenic acid (C) relative to 100 parts by weight in total of the fluoroaluminosilicate glass particles (A), the basic calcium phosphate particles (B1), and the acidic calcium phosphate particles (B2). When the content of the polyalkenic acid (C) is less than 10 parts by weight, sufficient mechanical strength may not be attained because a three-dimensional network structure resulting from a glass ionomer reaction cannot be formed sufficiently. Accordingly, the content is more preferably 13 parts by weight or more, particularly preferably 18 parts by weight or more. On the other hand, when the content of the polyalkenic acid (C) exceeds 40 parts by weight, this amount exceeds an amount required to form a three-dimensional network structure via a glass ionomer reaction with the fluoroaluminosilicate glass particles (A), and as a result, excess polyalkenic acid (C) which does not contribute to curing may cause curing defect. Moreover, it may become difficult to perform kneading due to excessively high viscosity at the time of kneading. The blending amount of the polyalkenic acid (C) is more preferably 30 parts by weight or less, particularly preferably 27 parts by weight or less.

The polyalkenic acid (C) to be used for the present invention is not particularly restricted, and refers to a polymer of an unsaturated monocarboxylic acid or an unsaturated dicarboxylic acid. Examples of the polyalkenic acid include homopolymers of acrylic acid, methacrylic acid, 2-chloroacrylic acid, 2-cyanoacrylic acid, aconitic acid, mesaconic acid, maleic acid, itaconic acid, fumaric acid, glutaconic acid, citraconic acid, utraconic acid; copolymers of two or more of these unsaturated carboxylic acids; and copolymers of these unsaturated carboxylic acids and copolymerizable monomers. These may be used individually or in combination. From the viewpoint of strength of adhesion to tooth substance and an increase in mechanical strength, at least one member selected from the group consisting of a copolymer of acrylic acid with maleic acid and a copolymer of acrylic acid with itaconic acid is more preferable, and a copolymer of acrylic acid with itaconic acid is particularly preferable. Moreover, a polymer with a weight average molecular weight of 5,000 to 50,000 containing no polymerizable ethylenically unsaturated double bonds is preferable. When the weight average molecular weight is less than 5,000, a cured product may tend to be low in strength and an adhesion force to tooth substance may lower. Accordingly, the weight average molecular weight is more preferably 10,000 or more, particularly preferably 35,000. When the weight average molecular weight exceeds 50,000, it may become difficult to perform kneading due to excessively high viscosity at the time of kneading. Accordingly, the weight average molecular weight is more preferably 45,000 or less, particularly preferably 40,000 or less.

The method for producing the polyalkenic acid (C) to be used for the present invention is not particularly restricted, and a commercial product may be used, if available. Particularly, in the case of adding the polyalkenic acid (C) to a powder agent, it is preferable to further pulverize a commercial product in many cases. In this case, a pulverizing apparatus such as a ball mill, a pestle and mortar machine, a jet mill, or a spray dryer may be used. Moreover, the polyalkenic acid (C) can also be obtained by pulverizing a polyalkenic acid powder together with a liquid medium such as alcohol, with the use of a pestle and mortar machine, a ball mill, or the like to prepare a slurry, and then drying the resulting slurry. At this time, a spray dryer is preferably used as a pulverizing apparatus.

Moreover, the polyalkenic acid (C) to be used for the present invention may be added in a powder form to be blended, or alternatively, may be blended after being added to a liquid agent. In either case, a curable composition can be formed. In the present invention, it is preferable to add the polyalkenic acid (C) to both of a powder agent and a liquid agent because this makes it possible to blend the polyalkenic acid (C) in a sufficient amount for securing adhesion to tooth substance and mechanical strength while maintaining a liquid agent at moderate viscosity.

The dental curable composition of the present invention is required to contain 0.3 to 10 parts by weight of the tartaric acid (D) relative to 100 parts by weight in total of the fluoroaluminosilicate glass particles (A), the basic calcium phosphate particles (B1), and the acidic calcium phosphate particles (B2). In the present invention, a prescribed amount of tartaric acid may be added for the purpose of regulating (delaying) the curing reaction between the above-described powder material and the acid component. Examples of tartaric acid preferable for this purpose include D-tartaric acid, L-tartaric acid, and DL-tartaric acid; however, L-tartaric acid is particularly preferable from the viewpoint of increase in strength and aesthetic quality of a resulting cured substance. When the content of the tartaric acid (D) is less than 0.3 parts by weight, it may not be possible to secure a sufficient operation time before kneading a powder agent and a liquid agent together and applying the resulting substance to a patient. Accordingly, the content is more preferably 1 part by weight or more, particularly preferably 2 parts by weight or more. On the other hand, when the content of the tartaric acid (D) exceeds 10 parts by weight, curing may not be attained within a clinically appropriate time due to delay of curing time. Accordingly, the content is more preferably 7 parts by weight or less, particularly preferably 5 parts by weight or less. The tartaric acid (D) may be added in the form of a powder or in the form of a liquid agent to be blended. Moreover, the tartaric acid (D) can also be blended by subjecting the fluoroaluminosilicate glass particles (A), the basic calcium phosphate particles (B1) and the acidic calcium phosphate particles (B2) to a surface treatment therewith.

The method for producing the tartaric acid (D) to be used for the present invention is not particularly restricted, and a commercial product may be used, if available. Particularly, in the case of adding the tartaric acid (D) to a powder agent, it is preferable to further pulverize a commercial product in many cases. In this case, a pulverizing apparatus such as a ball mill, a pestle and mortar machine, a jet mill, or a spray dryer may be used. Moreover, the tartaric acid (D) can be obtained by pulverizing a tartaric acid powder together with a liquid medium such as alcohol, with the use of a pestle and mortar machine, a ball mill, or the like to prepare a slurry, and then drying the resulting slurry.

The water (E) to be used for the present invention is an indispensable component in a liquid agent for obtaining the dental curable composition of the present invention. This is because in reaction in which a liquid agent and the fluoroaluminosilicate glass particles (A) serving as a main ingredient of a powder agent are mixed together to be cured, a neutralization reaction between the fluoroaluminosilicate glass particles (A) and the polyalkenic acid (C) advances in the presence of water. Further, a dental glass ionomer cement has a property to adhere to the surface of a tooth in the presence of water, so water is required to be present in the dental glass ionomer cement of the present invention.

The dental curable composition of the present invention is required to contain 10 to 90 parts by weight of the water (E) relative to 100 parts by weight in total of the fluoroaluminosilicate glass particles (A), the basic calcium phosphate particles (B1), and the acidic calcium phosphate particles (B2). When the content of the water (E) is less than 10 parts by weight, sufficient mechanical strength may not be attained because a three-dimensional network structure resulting from a glass ionomer reaction cannot be formed sufficiently, and it may not be possible to cause a sufficient hydration reaction between the basic calcium phosphate particles (B1) and the acidic calcium phosphate particles (B2). Accordingly, the content is more preferably 13 parts by weight or more, particularly preferably 15 parts by weight or more. On the other hand, when the content of the water (E) exceeds 90 parts by weight, the contents of the fluoroaluminosilicate glass particles (A), the basic calcium phosphate particles (B1), and the acidic calcium phosphate particles (B2) in a paste after powder-liquid kneading decrease, and as a result, a cured substance may not be obtained. Moreover, even if a cured substance is formed, the strength of the cured substance itself may lower. The content of the water (E) is more preferably 40 parts by weight or less, particularly preferably 30 parts by weight or less.

The dental curable composition of the present invention may contain an X-ray contrast medium, as necessary. This is because the medium makes it possible to monitor an operation of filling a composition paste after powder-liquid kneading, or to trace the change after filling. Examples of the X-ray contrast medium include one or two or more selected from among barium sulfate, bismuth subcarbonate, bismuth oxide, zirconium oxide, ytterbium fluoride, iodoform, barium apatite, barium titanate, lanthanum glass, barium glass, strontium glass, etc. The X-ray contrast medium may be blended in a powder agent, may be blended in a liquid agent, or may be blended in a composition paste under kneading.

The dental curable composition of the present invention may be blended with a filler with which modification in flowability of a powder agent or an increase in mechanical strength of a cured substance can be expected. As to the filler, a single kind of filler may be blended, or alternatively two or more kinds of fillers may be blended in combination. Examples of the filler include silica-based minerals such as kaolin, clay and mica; silica-based ceramics containing $Al_2O_3$, $B_2O_3$, $TiO_2$, $ZrO_2$, BaO, $La_2O_3$, SrO, ZnO, CaO, $P_2O_5$, $Li_2O$, $Na_2O$ or the like; and glass. As the glass, soda glass, lithium borosilicate glass, zinc glass, borosilicate glass, or bioglass is preferably used. Crystal quartz, alumina, titanium oxide, yttrium oxide, or aluminum hydroxide is also preferably used.

A pigment may be blended for the purpose of giving a prescribed color tone to the dental curable composition of the present invention and improving aesthetic qualities. Examples of the pigment to be blended include an organic pigment (coloring pigment) made of a synthetic organic dye or a natural organic dye, and an inorganic pigment obtained from a synthetic mineral or a natural mineral. Discoloration due to hydrogen sulfide is remarkably observed when an inorganic pigment is blended, whereas almost no such discoloration is observed when an organic pigment is blended. Therefore, an organic pigment is preferable which is not susceptible to an action of hydrogen sulfide that is believed to be a cause of discoloration in the oral cavity.

Examples of the organic pigment include New Coccine, Quinoline Yellow WS (trade names, both produced by Benifuji Chemical Industry Co., Ltd.), PV Fast Red BNP, Graphtol Yellow 3GP (trade names, both produced by Clariant (Japan) K.K.), Fast Green FCF (trade name, produced by KANTO CHEMICAL CO., INC.), Blue 404 (trade name, produced by Daito Kasei Kogyo Co., Ltd.), Yellow 8GNP, Yellow 3GNP, Yellow GRP, Yellow 3RLP, Red 2020, Red 2030, Red BRN, Red BRNP, and Red BN (trade names, produced by Ciba Specialty Chemicals Inc.).

An inorganic pigment may be used together with an organic pigment in an amount such that discoloration is not caused in order to impart a deep color tone peculiar to tooth substance to a crowning site to be restored. As the inorganic pigment, harmless pigments such as red oxide, zinc flower, titanium dioxide, carbon, and ultramarine are preferred, and an inherently black inorganic pigment (e.g., iron oxide) may be used in order to prevent blackening. Examples of a preferable inorganic pigment include KN-320, 100ED, and YELLOW-48 (trade names, produced by TODA KOGYO CORP.).

The method for producing the dental curable composition of the present invention is not in particularly restricted. The dental curable composition can be produced by mixing a powder agent comprising the fluoroaluminosilicate glass particles (A), the basic calcium phosphate particles (B1), and the acidic calcium phosphate particles (B2), with a liquid agent comprising the polyalkenic acid (C), the tartaric acid (D) and the water (E). The dental curable composition can also be produced by mixing a powder agent comprising the fluoroaluminosilicate glass particles (A), the basic calcium phosphate particles (B1), the acidic calcium phosphate particles (B2), and the polyalkenic acid (C), with a liquid agent comprising the tartaric acid (D) and the water (E). The dental curable composition can also be produced by mixing a powder agent comprising the fluoroaluminosilicate glass particles (A), the basic calcium phosphate particles (B1), the acidic calcium phosphate particles (B2), and the polyalkenic acid (C), with a liquid agent comprising the polyalkenic acid (C), the tartaric acid (D) and the water (E). The dental curable composition can also be produced by mixing a powder agent comprising the fluoroaluminosilicate glass particles (A), the basic calcium phosphate particles (B1), the acidic calcium phosphate particles (B2), the polyalkenic acid (C), and the tartaric acid (D), with a liquid agent comprising the polyalkenic acid (C) and the water (E). Among these, a method for producing a dental curable composition comprising mixing a powder agent comprising the fluoroaluminosilicate glass particles (A), the basic calcium phosphate particles (B1), the acidic calcium phosphate particles (B2), and the polyalkenic acid (C), with a liquid agent comprising the polyalkenic acid (C), the tartaric acid (D) and the water (E), or a method for producing a dental curable composition comprising a powder agent comprising the fluoroaluminosilicate glass particles (A), the basic calcium phosphate particles (B1), and the acidic calcium phosphate particles (B2), with a liquid agent comprising the polyalkenic acid (C), the tartaric acid (D) and the water (E) is preferably used, and a method for producing a dental curable composition comprising mixing a powder agent comprising the fluoroaluminosilicate glass particles (A), the basic calcium phosphate particles (B1), the acidic calcium phosphate particles (B2), and the polyalkenic acid (C), with a liquid agent comprising the polyalkenic acid (C), the tartaric acid (D) and the water (E) is more preferably used.

In the method for producing a dental curable composition of the present invention, the weight ratio (X/Y) of the powder agent (X) to the liquid agent (Y) is preferably from 1.0 to 5.0. This makes it possible to sufficiently develop performances such as powder-liquid kneadability and mechanical strength as a glass ionomer cement. The weight ratio (X/Y) of the powder agent (X) to the liquid agent (Y) is more preferably from 1.5 to 4.5, even more preferably from 1.8 to 3.8.

Accordingly, it is a preferable embodiment of the present invention to provide a method for producing a dental curable composition, the method comprising mixing a powder agent (X) comprising at least the fluoroaluminosilicate glass particles (A), the basic calcium phosphate particles (B1), and the acidic calcium phosphate particles (B2), with a liquid agent (Y) comprising at least the polyalkenic acid (C), the tartaric acid (D), and the water (E), wherein the weight ratio (X/Y) of the powder agent (X) to the liquid agent (Y) is from 1.0 to 5.0.

The fluoroaluminosilicate glass particles (A) and the polyalkenic acid (C) react together to be cured in the presence of the water (E), and hydroxyapatite is formed as a result of a hydration reaction of the basic calcium phosphate particles (B1) and the acidic calcium phosphate particles (B2), so that it is not possible to mix the fluoroaluminosilicate glass particles (A), the basic calcium phosphate particles (B1), the acidic calcium phosphate particles (B2), the polyalkenic acid (C), the tartaric acid (D) and the water (E) together beforehand, and to store the mixture in the form of a dental curable composition. From such a point of view, it is one of embodiments of the present invention to provide a dental curable composition kit comprising a powder agent comprising the fluoroaluminosilicate glass particles (A), the basic calcium phosphate particles (B1), and the acidic calcium phosphate particles (B2); and a liquid agent comprising the polyalkenic acid (C), the tartaric acid (D), and the water (E). It is one of embodiments of the present invention to provide a dental curable composition kit comprising a powder agent comprising the fluoroaluminosilicate glass particles (A), the basic calcium phosphate particles (B1), the acidic calcium phosphate particles (B2), and the polyalkenic acid (C); and a liquid agent comprising the tartaric acid (D) and the water (E). It is one of embodiments of the present invention to provide a dental curable composition kit comprising a powder agent comprising the fluoroaluminosilicate glass particles (A), the basic calcium phosphate particles (B1), the acidic calcium phosphate particles (B2), and the polyalkenic acid (C); and a liquid agent comprising the polyalkenic acid (C), the tartaric acid (D), and the water (E). It is one of embodiments of the present invention to provide a dental curable composition kit comprising a powder agent comprising the fluoroaluminosilicate glass particles (A), the basic calcium phosphate particles (B1), the acidic calcium phosphate particles (B2), the polyalkenic acid (C), and the tartaric acid (D); and a liquid agent comprising the polyalkenic acid (C) and the water (E). Among these, a dental curable composition kit comprising a powder agent comprising the fluoroaluminosilicate glass particles (A), the basic calcium phosphate particles (B1), the acidic calcium phosphate particles (B2), and the polyalkenic acid (C); and a liquid agent comprising the polyalkenic acid (C), the tartaric acid (D), and the water (E), or a dental curable composition kit comprising a powder agent comprising the fluoroaluminosilicate glass particles (A), the basic calcium phosphate particles (B1), and the acidic calcium phosphate particles (B2); and a liquid agent comprising the polyalkenic acid (C), the tartaric acid (D), and the water (E) is preferably used, and a dental curable composition kit comprising a powder agent comprising the fluoroaluminosilicate glass particles (A), the basic calcium phosphate particles (B1), the acidic calcium phosphate particles (B2), and the polyalkenic acid (C); and a liquid agent comprising a the polyalkenic acid (C), the tartaric acid (D), and the water (E) is more preferably used.

In the dental curable composition kit of the present invention, the powder agent (X) and the liquid agent (Y) are preferably used by mixing in a weight ratio (X/Y) within the range of from 1.0 to 5.0. This makes it possible to sufficiently develop performances such as powder-liquid kneadability and mechanical strength as a glass ionomer cement. It is preferable to use the powder agent (X) and the liquid agent (Y) by mixing in a weight ratio (X/Y) within the range of from 1.5 to 4.5, more preferably within the range of from 1.8 to 3.8.

Accordingly, it is a preferable embodiment of the present invention to provide a dental curable composition kit comprising: a powder agent (X) comprising at least the fluoroaluminosilicate glass particles (A), the basic calcium phosphate particles (B1), and the acidic calcium phosphate particles (B2); and a liquid agent (Y) comprising at least the polyalkenic acid (C), the tartaric acid (D), and the water (E), wherein the powder agent (X) and the liquid agent (Y) are mixed in a weight ratio (X/Y) within the range of from 1.0 to 5.0. The dental curable composition of the present invention is preferably used as a glass ionomer cement.

EXAMPLES

Hereafter, the present invention is described concretely with reference to Examples. In Examples, as to each of the average particle sizes of fluoroaluminosilicate glass particles (A), basic calcium phosphate particles (B1), acidic calcium phosphate particles (B2), a polyalkenic acid (C), and tartaric acid (D), measurement was conducted using a laser diffraction type particle size distribution analyzer ("SALD-2100" manufactured by Shimadzu Corporation), and a median diameter calculated from the result of the measurement was defined as an average particle size.

[Preparation of Powder Agent and Liquid Agent for Glass Ionomer Cement]

(1) Preparation of Fluoroaluminosilicate Glass Particles (A)

The fluoroaluminosilicate glass particles (A) were obtained by pulverizing commercially available fluoroaluminosilicate glass (G018-117, produced by SCHOTT, average particle size=40.0 μm) by the method described below.

Fluoroaluminosilicate glass particles having an average particle size of 30 μm were obtained by adding 100 g of commercially available fluoroaluminosilicate glass (G018-117, produced by SCHOTT, average particle size=40.0 μm) and 200 g of zirconia balls having a diameter of 20 mm to a 400-ml pulverization pot made of alumina ("Type A-3 HD Pot Mill" manufactured by Nikkato Corporation), followed by pulverization at a rotation speed of 150 rpm for 5 hours.

Fluoroaluminosilicate glass particles having an average particle size of 4 μm were obtained by adding 100 g of commercially available fluoroaluminosilicate glass (G018-117, produced by SCHOTT, average particle size=40.0 μm) and 200 g of zirconia balls having a diameter of 20 mm to a 400-ml pulverization pot made of alumina ("Type A-3 HD Pot Mill" manufactured by Nikkato Corporation), followed by pulverization at a rotation speed of 150 rpm for 15 hours.

Fluoroaluminosilicate glass particles having an average particle size of 0.5 μm were obtained by treating once commercially available fluoroaluminosilicate glass (G018-117, produced by SCHOTT, average particle size=40.0 μm) with a Nano Jetmizer (NJ-100, manufactured by Aishin Nano Technologies CO., LTD.) under a pulverization pressure condition of raw material supply pressure=0.7 MPa/pulverization pressure=0.7 MPa and a treatment amount condition of 8 kg/hr.

(2) Preparation of Basic Calcium Phosphate Particles (B1)

The basic calcium phosphate particles (B1) to be used for Examples were obtained by pulverizing crude tetracalcium phosphate prepared as follows. A cake-like equimolar mixture, which was obtained by adding commercially available particles of anhydrous calcium monohydrogen phosphate (Product No. 1430, J. T. Baker Chemical Co., N.J.) and calcium carbonate (Product No. 1288, J. T. Baker Chemical Co., N.J.) to water so as to be equimolar and stirring for 1 hour, followed by filtering and drying, was heated in an electric furnace (FUS732PB, manufactured by Advantec Toyo Kaisha, Ltd.) at 1500° C. for 24 hours, and then cooled in a desiccator to room temperature, so that lumps of tetracalcium phosphate were prepared. Moreover, the lumps were subjected to rough crushing in a mortar and subsequent sieving, a fine powder and the lumps of tetracalcium phosphate were removed, and the particle size was adjusted to a range of from 0.5 to 3 mm. Thus, crude tetracalcium phosphate was obtained.

Tetracalcium phosphate particles having an average particle size of 30 µm were obtained by adding 100 g of the crude tetracalcium phosphate and 200 g of zirconia balls having a diameter of 20 mm to a 400-ml pulverization pot made of alumina ("Type A-3 HD Pot Mill" manufactured by Nikkato Corporation), followed by pulverization at a rotation speed of 150 rpm for 5 hours.

Particles of tetracalcium phosphate having an average particle size of 19.0 µm were obtained by adding 100 g of the crude tetracalcium phosphate and 200 g of zirconia balls having a diameter of 20 mm to a 400-ml pulverization pot made of alumina ("Type A-3 HD Pot Mill" manufactured by Nikkato Corporation), followed by pulverization at a rotation speed of 150 rpm for 15 hours.

Particles of tetracalcium phosphate having an average particle size of 5.0 µm were obtained by treating once the crude tetracalcium phosphate with a Nano Jetmizer (NJ-100, manufactured by Aishin Nano Technologies CO., LTD.) under a pulverization pressure condition of raw material supply pressure=0.7 MPa/pulverization pressure=0.7 MPa and a treatment amount condition of 8 kg/hr.

(3) Preparation of Acidic Calcium Phosphate Particles (B2)

Particles of anhydrous calcium monohydrogen phosphate (B2) to be used for Examples were obtained by pulverizing commercially available particles of anhydrous calcium monohydrogen phosphate (produced by TAIHEI CHEMICAL INDUSTRIAL CO., LTD., average particle size=15.0 µm) by the method described below.

Particles of anhydrous calcium monohydrogen phosphate having an average particle size of 5.0 µm were obtained as follows. A slurry was obtained by adding 50 g of commercially available particles of anhydrous calcium monohydrogen phosphate (produced by TAIHEI CHEMICAL INDUSTRIAL CO., LTD., average particle size=15.0 µm), 120 g of 95% ethanol ("Ethanol (95)" produced by Wako Pure Chemical Industries, Ltd.) and 240 g of zirconia balls having a diameter of 10 mm to a 400-ml pulverization pot made of alumina ("Type A-3 HD Pot Mill" manufactured by Nikkato Corporation), followed by wet pulverization at a rotation speed of 120 rpm for 24 hours. The slurry was subjected to evaporation of ethanol with a rotary evaporator, followed by drying at 60° C. for 6 hours and additional vacuum drying at 60° C. for 12 hours.

Particles of anhydrous calcium monohydrogen phosphate having an average particle size of 1.0 µm were obtained as follows. A slurry was obtained by adding 50 g of commercially available particles of anhydrous calcium monohydrogen phosphate (produced by TAIHEI CHEMICAL INDUSTRIAL CO., LTD., average particle size=15.0 µm), 120 g of 95% ethanol ("Ethanol (95)" produced by Wako Pure Chemical Industries, Ltd.) and 240 g of zirconia balls having a diameter of 10 mm to a 400-ml pulverization pot made of alumina ("Type A-3 HD Pot Mill" manufactured by Nikkato Corporation), followed by wet pulverization at a rotation speed of 120 rpm for 24 hours. The slurry was subjected to evaporation of ethanol with a rotary evaporator, followed by drying at 60° C. for 6 hours and additional vacuum drying at 60° C. for 24 hours.

Particles of anhydrous calcium monohydrogen phosphate having an average particle size of 0.5 µm were obtained by treating once commercially available particles of anhydrous calcium monohydrogen phosphate (produced by TAIHEI CHEMICAL INDUSTRIAL CO., LTD., average particle size=15.0 µm) with a Nano Jetmizer (NJ-100, manufactured by Aishin Nano Technologies CO., LTD.) under a pulverization pressure condition of raw material supply pressure=0.7 MPa/pulverization pressure=0.7 MPa and a treatment amount condition of 8 kg/hr.

As to particles of tricalcium phosphate having an average particle size of 1 µm, commercially available tricalcium α-phosphate (produced by TAIHEI CHEMICAL INDUSTRIAL CO., LTD.) was used as it was.

As to particles of anhydrous calcium dihydrogen phosphate having an average particle size of 1 µm, commercially available anhydrous calcium dihydrogen phosphate (produced by TAIHEI CHEMICAL INDUSTRIAL CO., LTD.) was used as it was.

(4) Preparation of Polyalkenic Acid (C)

A commercially available polyalkenic acid (produced by Nissei Kagaku Kogyo) was used as it was when adding the polyalkenic acid (C) to a liquid agent, whereas the polyalkenic acid (C) was used after pulverization by the method described below when adding the polyalkenic acid (C) to a powder agent.

A polyalkenic acid powder was obtained by treating once a commercially available polyalkenic acid (produced by Nissei Kagaku Kogyo) with a Nano Jetmizer (NJ-100, manufactured by Aishin Nano Technologies CO., LTD.) under a pulverization pressure condition of raw material supply pressure=0.7 MPa/pulverization pressure=0.7 MPa and a treatment amount condition of 8 kg/hr. The resulting polyalkenic acid powder had an average particle size of 3 µm.

(5) Preparation of Tartaric Acid (D)

As to the tartaric acid (D), commercially available L-tartaric acid (produced by Iwata Chemical Co., Ltd.) was used as it was. However, only when adding the tartaric acid (D) to a powder agent, tartaric acid (D) pulverized with an agate mortar for about one hour so as to have an average particle size of from 15 to 25 µm was used only when added to a powder product.

(6) Preparation of Water (E)

As to the water (E), commercially available purified water in the Japanese Pharmacopoeia (produced by Takasugi Pharmaceutical Co., Ltd.) was used as it was.

(7) Preparation of Powder Agent

A powder agent was obtained by adding to a high-speed rotation mill ("SM-1" manufactured by AS-ONE Corporation) the fluoroaluminosilicate glass particles (A), the basic calcium phosphate particles (B1), the acidic calcium phosphate particles (B2), and as necessary the polyalkenic acid powder (C) and the tartaric acid (D) weighed with composition given in Tables 1 to 4, and mixing the components at a rotation speed of 1000 rpm for 3 minutes.

(8) Preparation of Liquid Agent

A liquid agent was prepared by stirring the polyalkenic acid powder (C) (produced by Nissei Kagaku Kogyo), the L-tartaric acid (D) (produced by Iwata Chemical Co., Ltd.) and the water (E) weighed with composition given in Tables 1 to 4 with a magnetic stirrer for 24 hours.

[Compressive Strength Test]

(1) Preparation of Sample for Compressive Strength Measurement

A paste was prepared by weighing out 0.5 g of a powder agent having composition given in Tables 1 to 4, and adding thereonto a liquid agent having composition given in Tables 1 to 4 so as to have a powder-liquid weight ratio given in Tables 1 to 4, followed by kneading. A separable stainless steel mold having a diameter of 6 mm and a depth of 3 mm was put on a smooth glass plate, and the paste was filled therein while taking care not to allow gas to be contained, and then a composition paste was molded (n=9) by compressing the smooth glass plate from above with a smooth glass plate. Thereafter, incubation was performed for one hour in an environment of 37° C. and a relative humidity of 100%, and then a cured substance was removed from the mold. The cured substance was immersed in 150 ml of distilled water at 37° C., and was additionally held for 20 hours or 30 days. Thereafter, the compressive strength (MPa) of the cured substance was measured (n=9) by applying a load at a rate of 0.75 mm/min in the axial direction of a cylindrical cured substance with the use of a dynamic strength analyzer ("AG-1 100 kN" manufactured by Shimadzu Corporation) in accordance with the method described in JIS T6609-1. Hereinafter, compressive strength after 20 hours may be referred to as initial compressive strength.

(2) Method of Calculating Increase in Compressive Strength

An increase in compressive strength was calculated using the following formula.

Increase in compressive strength (MPa)=(compressive strength after 30 days (MPa))−compressive strength after 20 hours (MPa))

[Operability]
(1) Operability

A paste was prepared by weighing out 0.1 g of a powder agent having composition given in Tables 1 to 4, adding thereonto a liquid agent having composition given in Tables 1 to 4 so as to have a powder-liquid weight ratio given in Tables 1 to 4, and then kneading the mixture for 30 seconds on a kneading paper (85×115 mm). Regarding the properties of the paste, operability was evaluated in accordance with the evaluation criteria described below.

(2) Criteria for Operability Evaluation

A: The powder agent and the liquid agent exhibit a good affinity just after the start of kneading, and a paste can be obtained by kneading the mixture for 20 seconds with a kneading spatula for dental use. The resulting paste exhibits good spreading and no sandy feeling.

B: Although the powder agent and the liquid agent exhibit a little poor affinity just after the start of kneading, a paste can be obtained by kneading the mixture for 20 seconds with a kneading spatula for dental use. The paste exhibits good spreading, but small sandy feeling may be provided during kneading.

C: The powder agent and the liquid agent exhibit a poor affinity just after the start of kneading, and it requires 30 seconds for kneading the mixture with a kneading spatula for dental use in order to obtain a paste. The paste exhibits good spreading, but small sandy feeling may be provided during kneading.

D: The powder agent and the liquid agent exhibit a poor affinity just after the start of kneading, and it requires 30 seconds or more for kneading the mixture with a kneading spatula for dental use in order to obtain a paste, or kneading cannot be performed. When kneading can be performed, the resulting paste exhibits poor spreading and is cured on a kneading paper within two minutes, so that an operation time cannot be secured. Moreover, sandy feeling may be provided during kneading.

Criteria from A to C are allowable for practical use.

[Preparation of Bovine Tooth for Remineralization]

A cheek-side center of a healthy bovine incisor tooth was ground with #80, #1000 sand papers by using a rotary grinder, so that a dentin was exposed. The ground surface of the bovine tooth was further polished with wrapping films (#1200, #3000, #8000, produced by Sumitomo 3M Ltd.) to be smoothened. This dentin portion was masked with manicure with a window of a test portion as large as 7 mm in both the ordinate direction and the abscissa direction (hereinafter referred to as a "dentin window") left unmasked and was air-dried for one hour. This bovine tooth was demineralized by immersing the bovine tooth for one week in 150 ml of a 50 mM demineralization solution prepared by diluting acetic acid (produced by Wako Pure Chemical Industries, Ltd.) with distilled water, and then washing the tooth with water for 30 minutes or more, so that a bovine tooth to be used for a remineralization test was prepared.

[Preparation of Artificial Saliva]

Sodium chloride (8.77 g, 150 mmol), potassium dihydrogen phosphate (122 mg, 0.9 mmol), calcium chloride (166 mg, 1.5 mmol), and Hepes (4.77 g, 20 mmol) were separately weighed out on weighing dishes, and then added one after another to a 2000-ml beaker containing about 800 ml of distilled water. After confirmation of complete dissolution of the solutes, pH was adjusted to 7.0 by dropping a 10% aqueous sodium hydroxide solution while measuring the acidity of the solution with a pH meter (F55, manufactured by HORIBA, Ltd.). Subsequently, this solution was added to a 1000-ml volumetric flask and diluted, so that 1000 ml of artificial saliva was obtained.

[Remineralization Test]

The bovine tooth for remineralization prepared above was immersed in distilled water and left to stand for 30 minutes, and then about 0.1 g of a paste obtained by kneading a powder agent and a liquid agent with a prescribed powder-liquid ratio given in Tables 1 to 4 on a kneading paper was applied to a half of a dentin window, and then incubated under conditions of 37° C. and 100% RH for 60 minutes to be cured. Thereafter, the sample was stored in the artificial saliva at 37° C. for two weeks with a cured substance being attached to the bovine tooth for a remineralization test. The artificial saliva was changed every day (n=5).

[Remineralization Capability Evaluation]
(1) Preparation of Epoxy Resin

The preparation of an epoxy resin was performed in accordance with the Luft method, and a method was used which comprises mixing an epoxy resin and a curing agent uniformly and then adding an accelerator. To a 100-ml disposable cup, 41 ml of Luveak 812 (epoxy resin, produced by Nacalai Tesque, Inc.), 31 ml of Luveak MNA (curing agent, produced by Nacalai Tesque, Inc.), and 10 ml of Luveak DDSA (curing agent, produced by Nacalai Tesque, Inc.) were measured with disposable syringes, respectively, and added, followed by stirring for 10 minutes. To the resultant was dropped slowly under stirring 1.2 ml of Luveak DMP-30 (accelerator, produced by Nacalai Tesque, Inc.) measured in a disposable syringe, and stirring was continued for additional 10 minutes after the addition, thereby completing the preparation.

(2) Production of Sample for Hardness Measurement

The mineralized bovine tooth was removed from the artificial saliva and was washed with water, and then it was immersed into a 70% aqueous ethanol solution contained in a vial. Immediately after the immersion, the vial was moved into a desiccator and was placed under a reduced pressure condition for 10 minutes. Then, the vial was taken out from the desiccator and it was attached to a low-speed stirrer (TR-118, manufactured by AS-ONE Corporation), followed by stirring at a rotation speed of about 4 rpm for 1 hour. The same operations were performed using a 80% aqueous ethanol solution, a 90% aqueous ethanol solution, a 99% aqueous ethanol solution, and 100% ethanol (twice), wherein the bovine tooth was immersed in the second 100% ethanol continuously for one night. Next day, the same operations were carried out sequentially for a 1:1 mixed solvent of propylene oxide and ethanol and for 100% propylene oxide (twice), wherein the bovine tooth was immersed in the second propylene oxide continuously for one night. Moreover, the same operations were carried out also for a mixed solution of epoxy resin:propylene oxide=1:1, a mixed solution of epoxy resin:propylene oxide=4:1, and 100% epoxy resin (twice). As for these, the immersion time was determined to be two hours. Finally, the bovine tooth sample was put into a plastic container in which an epoxy resin was contained, and a curing reaction was carried out at 45° C. for one day and at 60° C. for two days. After the completion of the curing, the sample was cut together with the polyethylene container along a direction perpendicular to a demineralized surface by using a precision low-speed cutter (ISOMET1000, manufactured by BUEHLER), so that a slice of about 1 mm in thickness having a cross section of a portion to be tested was obtained. This slice was polished with wrapping films (#1200, #3000, #8000, produced by Sumitomo 3M Ltd.) to form a sample for hardness measurement (n=5).

(3) Hardness Measurement

Hardness was measured on cross sections of a demineralized part and a remineralized part with a load of 2 mN by using a nano indentor (ENT-1100a, manufactured by ELIONIX INC.). An operation of measuring hardnesses at 10 points with 40-μm intervals in the depth direction from the surface layer was carried out on three rows in each of the demineralized part and the remineralized part, and an average value of the hardnesses at each depth was calculated. Moreover, hardnesses were measured as a control at three points also for undemineralized healthy dentin having a depth of 600 μm, and an average value of the hardnesses was calculated. Remineralization capability was quantified as a hardness recovery ratio by the following formula.

Hardness recovery ratio (%)=[(average value of hardness at a 360-μm depth of remineralized part)−(average value of hardness at a 360-μm depth of demineralized part)]/(average value of hardness of healthy dentin)×100

Examples 1 to 42

Dental curable compositions were prepared with composition given in Tables 1 to 4 by the procedures described above, and then the operability, compressive strength, and remineralization capability of each dental curable composition were evaluated. The evaluation results obtained are summarized in Tables 1 to 4.

Comparative Examples 1 to 10

Compositions were prepared with composition given in Table 4 by the procedures described above, and then the operability, compressive strength, and remineralization capability of each composition were evaluated. The evaluation results obtained are summarized in Table 4. The hydroxyapatite particles used for Comparative Example 10 were commercially available hydroxyapatite (HAP-100, produced by TAIHEI CHEMICAL INDUSTRIAL CO., LTD.), which was used as it was.

TABLE 1

| | | | | Example 1 | Example 2 | Example 3 | Example 4 | Example 5 | Example 6 | Example 7 |
|---|---|---|---|---|---|---|---|---|---|---|
| Powder agent | A | Fluoroaluminosilicate glass (D50: 0.5 μm) | (part(s) by weight) | | | | | | | |
| | | Fluoroaluminosilicate glass (D50: 4 μm) | (part(s) by weight) | 89.6 | 86.0 | 81.5 | 72.4 | 86.0 | 86.0 | 86.0 |
| | | Fluoroaluminosilicate glass (D50: 30 μm) | (part(s) by weight) | | | | | | | |
| | B1 | Tetracalcium phosphate (D50: 5 μm) | (part(s) by weight) | | | | | | | |
| | | Tetracalcium phosphate (D50: 19 μm) | (part(s) by weight) | 0.7 | 3.3 | 6.6 | 13.2 | 1.7 | 3.3 | 3.3 |
| | | Tetracalcium phosphate (D50: 30 μm) | (part(s) by weight) | | | | | | | |
| | B2 | Anhydrous calcium monohydrogen phosphate (D50: 0.5 μm) | (part(s) by weight) | | | | | | | |
| | | Anhydrous calcium monohydrogen phosphate (D50: 1 μm) | (part(s) by weight) | 0.2 | 1.2 | 2.5 | 4.9 | | 1.2 | 1.2 |
| | | Anhydrous calcium monohydrogen phosphate (D50: 5 μm) | (part(s) by weight) | | | | | | | |
| | | Tricalcium phosphate (D50: 1 μm) | (part(s) by weight) | | | | | 2.8 | | |
| | | Anhydrous calcium dihydrogen phosphate (D50: 1 μm) | (part(s) by weight) | | | | | | | |
| | — | Hydroxyapatite | (part(s) by weight) | | | | | | | |
| | D | L-tartaric acid | (part(s) by weight) | | | | | | | |
| | C | Polyalkenic acid powder (acrylic acid/itaconic acid copolymer) | (part(s) by weight) | 9.5 | 9.5 | 9.5 | 9.5 | 9.5 | 9.5 | 9.5 |
| Total | | | (part(s) by weight) | 100.0 | 100.0 | 100.0 | 100.0 | 100.0 | 100.0 | 100.0 |
| Liquid agent | C | Polyalkenic acid (acrylic acid/itaconic acid copolymer) | (part(s) by weight) | 30.1 | 30.1 | 30.1 | 30.1 | 30.1 | 30.1 | 30.1 |
| | D | L-tartaric acid | (part(s) by weight) | 8.9 | 8.9 | 8.9 | 8.9 | 8.9 | 1.0 | 15.0 |

TABLE 1-continued

| | | | | | | | | | | |
|---|---|---|---|---|---|---|---|---|---|---|
| E | Water | (part(s) by weight) | 61.0 | 61.0 | 61.0 | 61.0 | 61.0 | 68.9 | 54.9 |
| Total | | (part(s) by weight) | 100.0 | 100.0 | 100.0 | 100.0 | 100.0 | 100.0 | 100.0 |
| Powder-liquid weight ratio | | | 2.3 | 2.3 | 2.3 | 2.3 | 2.3 | 2.3 | 2.3 |
| Operability | | | A | A | A | B | A | B | A |
| Initial compressive strength | | (MPa) | 125.7 | 135.2 | 132.0 | 119.9 | 123.9 | 126.2 | 120.8 |
| Compressive strength after 30 days | | (MPa) | 145.6 | 170.9 | 167.4 | 145.3 | 150.1 | 153.1 | 150.4 |
| Increase in compressive strength for 30 days | | (MPa) | 19.9 | 35.7 | 35.4 | 25.4 | 26.2 | 26.9 | 29.6 |
| Hardness recovery ratio | | (%) | 15 | 43 | 41 | 43 | 30 | 38 | 38 |
| Content of A relative to 100 parts by weight in total of A + B1 + B2 | | (part(s) by weight) | 99 | 95 | 90 | 80 | 95 | 95 | 95 |
| Total content of B1 and B2 relative to 100 parts by weight of in total A + B1 + B2 | | (part(s) by weight) | 1 | 5 | 10 | 20 | 5 | 5 | 5 |
| Content of C relative to 100 parts by weight in total of A + B1 + B2 | | (part(s) by weight) | 25.0 | 25.0 | 25.0 | 25.0 | 25 | 25.0 | 25.0 |
| Content of D relative to 100 parts by weight in total of A + B1 + B2 | | (part(s) by weight) | 4.3 | 4.3 | 4.3 | 4.3 | 4 | 0.5 | 7.2 |
| Content of E relative to 100 parts by weight in total of A + B1 + B2 | | (part(s) by weight) | 29.3 | 29.3 | 29.3 | 29.3 | 29 | 33.1 | 26.4 |
| Ca/P ratio | | | 1.67 | 1.67 | 1.67 | 1.67 | 1.67 | 1.67 | 1.67 |

| | | | | Example 8 | Example 9 | Example 10 | Example 11 | Example 12 | Example 13 |
|---|---|---|---|---|---|---|---|---|---|
| Powder agent | A | Fluoroaluminosilicate glass (D50: 0.5 μm) | (part(s) by weight) | | | | | 86.0 | |
| | | Fluoroaluminosilicate glass (D50: 4 μm) | (part(s) by weight) | 95.1 | 95.1 | 71.3 | 79.2 | | |
| | | Fluoroaluminosilicate glass (D50: 30 μm) | (part(s) by weight) | | | | | | 86.0 |
| | B1 | Tetracalcium phosphate (D50: 5 μm) | (part(s) by weight) | | | | | | |
| | | Tetracalcium phosphate (D50: 19 μm) | (part(s) by weight) | 3.6 | 3.6 | 2.7 | 3.0 | 3.3 | 3.3 |
| | | Tetracalcium phosphate (D50: 30 μm) | (part(s) by weight) | | | | | | |
| | B2 | Anhydrous calcium monohydrogen phosphate (D50: 0.5 μm) | (part(s) by weight) | | | | | | |
| | | Anhydrous calcium monohydrogen phosphate (D50: 1 μm) | (part(s) by weight) | 1.3 | 1.3 | 1.0 | 1.1 | 1.2 | 1.2 |
| | | Anhydrous calcium monohydrogen phosphate (D50: 5 μm) | (part(s) by weight) | | | | | | |
| | | Tricalcium phosphate (D50: 1 μm) | (part(s) by weight) | | | | | | |
| | | Anhydrous calcium dihydrogen phosphate (D50: 1 μm) | (part(s) by weight) | | | | | | |
| | — | Hydroxyapatite | (part(s) by weight) | | | | | | |
| | D | L-tartaric acid | (part(s) by weight) | | | | | | |
| | C | Polyalkenic acid powder (acrylic acid/itaconic acid copolymer) | (part(s) by weight) | | 25.0 | 16.7 | 9.5 | 9.5 | |
| Total | | | (part(s) by weight) | 100.0 | 100.0 | 100.0 | 100.0 | 100.0 | 100.0 |
| Liquid agent | C | Polyalkenic acid (acrylic acid/itaconic acid copolymer) | (part(s) by weight) | 50.0 | 50.0 | | | 30.1 | 30.1 |
| | D | L-tartaric acid | (part(s) by weight) | 8.9 | 8.9 | 8.9 | 8.9 | 8.9 | 8.9 |
| | E | Water | (part(s) by weight) | 41.1 | 41.1 | 91.1 | 91.1 | 61.0 | 61.0 |
| Total | | | (part(s) by weight) | 100.0 | 100.0 | 100.0 | 100.0 | 100.0 | 100.0 |
| Powder-liquid weight ratio | | | | 1.5 | 4.0 | 4.0 | 1.5 | 2.3 | 2.3 |
| Operability | | | | C | C | B | A | B | B |
| Initial compressive strength | | | (MPa) | 83.0 | 180.2 | 201.9 | 81.8 | 120.8 | 131.0 |
| Compressive strength after 30 days | | | (MPa) | 108.4 | 205.3 | 223.0 | 99.7 | 146.9 | 160.4 |
| Increase in compressive strength for 30 days | | | (MPa) | 25.4 | 25.1 | 21.1 | 17.9 | 26.1 | 29.4 |
| Hardness recovery ratio | | | (%) | 37 | 35 | 37 | 34 | 40 | 41 |
| Content of A relative to 100 parts by weight in total of A + B1 + B2 | | | (part(s) by weight) | 95 | 95 | 95 | 95 | 95 | 95 |
| Total content of B1 and B2 relative to 100 parts by weight of in total A + B1 + B2 | | | (part(s) by weight) | 5 | 5 | 5 | 5 | 5 | 5 |
| Content of C relative to 100 parts by weight in total of A + B1 + B2 | | | (part(s) by weight) | 33.3 | 12.5 | 33.3 | 20.0 | 25.0 | 25.0 |

TABLE 1-continued

|  |  |  |  |  |  |  |  |
|---|---|---|---|---|---|---|---|
| Content of D relative to 100 parts by weight in total of A + B1 + B2 | (part(s) by weight) | 5.9 | 2.2 | 3.0 | 6.6 | 4.3 | 4.3 |
| Content of E relative to 100 parts by weight in total of A + B1 + B2 | (part(s) by weight) | 27.4 | 10.3 | 30.4 | 72.9 | 29.3 | 29.3 |
| Ca/P ratio |  | 1.67 | 1.67 | 1.67 | 1.67 | 1.67 | 1.67 |

TABLE 2

| | | | | Example 14 | Example 15 | Example 16 | Example 17 | Example 18 | Example 19 | Example 20 |
|---|---|---|---|---|---|---|---|---|---|---|
| Powder agent | A | Fluoroaluminosilicate glass (D50; 0.5 μm) | (part(s) by weight) | | | | | | | |
| | | Fluoroaluminosilicate glass (D50: 4 μm) | (part(s) by weight) | 86.0 | 86.0 | 86.0 | 86.0 | 86.0 | 86.0 | 86.0 |
| | | Fluoroaluminosilicate glass (D50: 30 μm) | (part(s) by weight) | | | | | | | |
| | B1 | Tetracalcium phosphate (D50: 5 μm) | (part(s) by weight) | 3.3 | | | | | | |
| | | Tetracalcium phosphate (D50: 19 μm) | (part(s) by weight) | | | 3.3 | 3.3 | 4.2 | 3.2 | 1.0 |
| | | Tetracalcium phosphate (D50: 30 μm) | (part(s) by weight) | | 3.3 | | | | | |
| | B2 | Anhydrous calcium monohydrogen phosphate (D50: 0.5 μm) | (part(s) by weight) | | | | | 1.2 | | |
| | | Anhydrous calcium monohydrogen phosphate (D50: 1 μm) | (part(s) by weight) | 1.2 | 1.2 | | | 0.3 | | 3.5 |
| | | Anhydrous calcium monohydrogen phosphate (D50: 5 μm) | (part(s) by weight) | | | | 1.2 | | | |
| | | Tricalcium phosphate (D50: 1 μm) | (part(s) by weight) | | | | | | | |
| | | Anhydrous calcium dihydrogen phosphate (D50: 1 μm) | (part(s) by weight) | | | | | | 1.3 | |
| | — | Hydroxyapatite | (part(s) by weight) | | | | | | | |
| | D | L-tartaric acid | (part(s) by weight) | | | | | | | |
| | C | Polyalkenic acid powder (acrylic acid/itaconic acid copolymer) | (part(s) by weight) | 9.5 | 9.5 | 9.5 | 9.5 | 9.5 | 9.5 | 9.5 |
| Total | | | (part(s) by weight) | 100.0 | 100.0 | 100.0 | 100.0 | 100.0 | 100.0 | 100.0 |
| Liquid agent | C | Polyalkenic acid (acrylic acid/itaconic acid copolymer) | (part(s) by weight) | 30.1 | 30.1 | 30.1 | 30.1 | 30.1 | 30.1 | 30.1 |
| | D | L-tartaric acid | (part(s) by weight) | 8.9 | 8.9 | 8.9 | 8.9 | 8.9 | 8.9 | 8.9 |
| | E | Water | (part(s) by weight) | 61.0 | 61.0 | 61.0 | 61.0 | 61.0 | 61.0 | 61.0 |
| Total | | | (part(s) by weight) | 100.0 | 100.0 | 100.0 | 100.0 | 100.0 | 100.0 | 100.0 |
| Powder-liquid weight ratio | | | | 2.3 | 2.3 | 2.3 | 2.3 | 2.3 | 2.3 | 2.3 |
| Operability | | | | A | B | A | A | A | A | A |
| Initial compressive strength | | | (MPa) | 128.5 | 126.9 | 130.2 | 122.2 | 121.9 | 120.3 | 127.2 |
| Compressive strength after 30 days | | | (MPa) | 153.2 | 153.0 | 158.9 | 149.8 | 139.9 | 138.4 | 143.8 |
| Increase in compressive strength for 30 days | | | (MPa) | 24.7 | 26.1 | 28.7 | 27.6 | 18.0 | 18.1 | 16.6 |
| Hardness recovery ratio | | | (%) | 41 | 39 | 42 | 41 | 24 | 32 | 23 |
| Content of A relative to 100 parts by weight in total of A + B1 + B2 | | | (part(s) by weight) | 95 | 95 | 95 | 95 | 95 | 95 | 95 |
| Total content of B1 and B2 relative to 100 parts by weight of in total A + B1 + B2 | | | (part(s) by weight) | 5 | 5 | 5 | 5 | 5 | 5 | 5 |
| Content of C relative to 100 parts by weight in total of A + B1 + B2 | | | (part(s) by weight) | 25.0 | 25.0 | 25.0 | 25.0 | 25.0 | 25.0 | 25.0 |
| Content of D relative to 100 parts by weight in total of A + B1 + B2 | | | (part(s) by weight) | 4.3 | 4.3 | 4.3 | 4.3 | 4.3 | 4.3 | 4.3 |
| Content of E relative to 100 parts by weight in total of A + B1 + B2 | | | (part(s) by weight) | 29.3 | 29.3 | 29.3 | 29.3 | 29.3 | 29.3 | 29.3 |
| Ca/P ratio | | | | 1.67 | 1.67 | 1.67 | 1.67 | 1.90 | 1.40 | 1.20 |

TABLE 2-continued

|  |  |  |  | Example 21 | Example 22 | Example 23 | Example 24 | Example 25 | Example 26 |
|---|---|---|---|---|---|---|---|---|---|
| Powder agent | A | Fluoroaluminosilicate glass (D50; 0.5 μm) | (part(s) by weight) |  |  |  |  |  |  |
|  |  | Fluoroaluminosilicate glass (D50; 4 μm) | (part(s) by weight) | 86.0 | 86.0 | 86.0 | 86.0 | 86.0 | 86.0 |
|  |  | Fluoroaluminosilicate glass (D50: 30 μm) | (part(s) by weight) |  |  |  |  |  |  |
|  | B1 | Tetracalcium phosphate (D50: 5 μm) | (part(s) by weight) |  |  |  |  |  |  |
|  |  | Tetracalcium phosphate (D50: 19 μm) | (part(s) by weight) | 3.3 | 3.3 | 3.3 | 3.3 | 3.3 | 3.3 |
|  |  | Tetracalcium phosphate (D50: 30 μm) | (part(s) by weight) |  |  |  |  |  |  |
|  | B2 | Anhydrous calcium monohydrogen phosphate (D50: 0.5 μm) | (part(s) by weight) |  |  |  |  |  |  |
|  |  | Anhydrous calcium monohydrogen phosphate (D50: 1 μm) | (part(s) by weight) | 1.2 | 1.2 | 1.2 | 1.2 | 1.2 | 1.2 |
|  |  | Anhydrous calcium monohydrogen phosphate (D50: 5 μm) | (part(s) by weight) |  |  |  |  |  |  |
|  |  | Tricalcium phosphate (D50: 1 μm) | (part(s) by weight) |  |  |  |  |  |  |
|  |  | Anhydrous calcium dihydrogen phosphate (D50: 1 μm) | (part(s) by weight) |  |  |  |  |  |  |
|  | — | Hydroxyapatite | (part(s) by weight) |  |  |  |  |  |  |
|  | D | L-tartaric acid | (part(s) by weight) |  |  |  |  |  |  |
|  | C | Polyalkenic acid powder (acrylic acid/itaconic acid copolymer) | (part(s) by weight) | 9.5 | 9.5 | 9.5 | 9.5 | 9.5 | 9.5 |
| Total |  |  | (part(s) by weight) | 100.0 | 100.0 | 100.0 | 100.0 | 100.0 | 100.0 |
| Liquid agent | C | Polyalkenic acid (acrylic acid/itaconic acid copolymer) | (part(s) by weight) | 30.1 | 30.1 | 30.1 | 30.1 | 30.1 | 30.1 |
|  | D | L-tartaric acid | (part(s) by weight) | 8.9 | 8.9 | 8.9 | 8.9 | 8.9 | 3.3 |
|  | E | Water | (part(s) by weight) | 61.0 | 61.0 | 61.0 | 61.0 | 61.0 | 66.6 |
| Total |  |  | (part(s) by weight) | 100.0 | 100.0 | 100.0 | 100.0 | 100.0 | 100.0 |
| Powder-liquid weight ratio |  |  |  | 1.0 | 1.5 | 3.5 | 4.0 | 5.0 | 3.5 |
| Operability |  |  |  | A | A | A | B | C | B |
| Initial compressive strength |  |  | (MPa) | 80.5 | 95.5 | 226.6 | 221.0 | 238.9 | 203.2 |
| Compressive strength after 30 days |  |  | (MPa) | 106.7 | 121.5 | 265.1 | 248.1 | 265.4 | 229.9 |
| Increase in compressive strength for 30 days |  |  | (MPa) | 26.2 | 26.0 | 38.5 | 27.1 | 26.5 | 26.7 |
| Hardness recovery ratio |  |  | (%) | 25 | 28 | 45 | 44 | 45 | 38 |
| Content of A relative to 100 parts by weight in total of A + B1 + B2 |  |  | (part(s) by weight) | 95 | 95 | 95 | 95 | 95 | 95 |
| Total content of B1 and B2 relative to 100 parts by weight of in total A + B1 + B2 |  |  | (part(s) by weight) | 5 | 5 | 5 | 5 | 5 | 5 |
| Content of C relative to 100 parts by weight in total of A + B1 + B2 |  |  | (part(s) by weight) | 36.9 | 32.7 | 20.0 | 18.8 | 17.1 | 20.0 |
| Content of D relative to 100 parts by weight in total of A + B1 + B2 |  |  | (part(s) by weight) | 9.4 | 6.6 | 2.8 | 2.5 | 1.2 | 1.0 |
| Content of E relative to 100 parts by weight in total of A + B1 + B2 |  |  | (part(s) by weight) | 64.2 | 29.3 | 19.3 | 19.3 | 13.5 | 21.0 |
| Ca/P ratio |  |  |  | 1.67 | 1.67 | 1.67 | 1.67 | 1.67 | 1.67 |

TABLE 3

|  |  |  |  | Example 27 | Example 28 | Example 29 | Example 30 | Example 31 | Example 32 | Example 33 |
|---|---|---|---|---|---|---|---|---|---|---|
| Powder agent | A | Fluoroaluminosilicate glass (D50: 0.5 μm) | (part(s) by weight) |  |  |  |  |  |  |  |
|  |  | Fluoroaluminosilicate glass (D50; 4 μm) | (part(s) by weight) | 86.0 | 86.0 | 83.5 | 95.1 | 84.2 | 82.8 | 70.6 |
|  |  | Fluoroaluminosilicate glass (D50: 30 μm) | (part(s) by weight) |  |  |  |  |  |  |  |
|  | BI | Tetracalcium phosphate (D50: 5 μm) | (part(s) by weight) |  |  |  |  |  |  |  |

TABLE 3-continued

| | | | | | | | | | | |
|---|---|---|---|---|---|---|---|---|---|---|
| | | Tetracalcium phosphate (D50: 19 μm) | (part(s) by weight) | 3.3 | 1.7 | 3.2 | 3.6 | 3.2 | 3.2 | 2.7 |
| | | Tetracalcium phosphate (D50: 30 μm) | (part(s) by weight) | | | | | | | |
| | B2 | Anhydrous calcium monohydrogen phosphate (D50: 0.5 μm) | (part(s) by weight) | | | | | | | |
| | | Anhydrous calcium monohydrogen phosphate (D50: 1 μm) | (part(s) by weight) | 1.2 | | 1.2 | 1.3 | 1.2 | 1.1 | 1.0 |
| | | Anhydrous calcium monohydrogen phosphate (D50: 5 μm) | (part(s) by weight) | | | | | | | |
| | | Tricalcium phosphate (D50: 1 μm) | (part(s) by weight) | | 2.8 | | | | | |
| | | Anhydrous calcium dihydrogen phosphate (D50: 1 μm) | (part(s) by weight) | | | | | | | |
| | — | Hydroxyapatite | (part(s) by weight) | | | | | | | |
| | D | L-tartaric acid | (part(s) by weight) | | | 2.6 | | | | |
| | C | Polyalkenic acid powder (acrylic acid/itaconic acid copolymer) | (part(s) by weight) | 9.5 | 9.5 | 9.5 | | 11.4 | 12.9 | 25.7 |
| Total | | | (part(s) by weight) | 100.0 | 100.0 | 100.0 | 100.0 | 100.0 | 100.0 | 100.0 |
| Liquid agent | C | Polyalkenic acid (acrylic acid/itaconic acid copolymer) | (part(s) by weight) | 30.1 | 30.1 | 30.1 | 45.0 | 50.0 | | |
| | D | L-tartaric acid | (part(s) by weight) | 11.5 | 8.9 | | 8.9 | 8.9 | 8.9 | 8.9 |
| | E | Water | (part(s) by weight) | 58.4 | 61.0 | 69.9 | 46.1 | 41.1 | 91.1 | 91.1 |
| Total | | | (part(s) by weight) | 100.0 | 100.0 | 100.0 | 100.0 | 100.0 | 100.0 | 100.0 |
| Powder-liquid weight ratio | | | | 3.5 | 3.5 | 3.5 | 3.5 | 3.5 | 3.5 | 3.5 |
| Operability | | | | A | A | A | C | B | A | C |
| Initial compressive strength | | | (MPa) | 208.1 | 200.4 | 202.3 | 160.5 | 200.5 | 183.2 | 203.9 |
| Compressive strength after 30 days | | | (MPa) | 233.2 | 229.7 | 234.0 | 192.4 | 233.6 | 214.8 | 234.1 |
| Increase in compressive strength for 30 days | | | (MPa) | 25.1 | 29.3 | 31.7 | 31.9 | 33.1 | 31.6 | 30.2 |
| Hardness recovery ratio | | | (%) | 38 | 33 | 41 | 37 | 39 | 38 | 38 |
| Content of A relative to 100 parts by weight in total of A + B1 + B2 | | | (part(s) by weight) | 95 | 95 | 95 | 95 | 95 | 95 | 95 |
| Total content of B1 and B2 relative to 100 parts by weight of in total A + B1 + B2 | | | (part(s) by weight) | 5 | 5 | 5 | 5 | 5 | 5 | 5 |
| Content of C relative to 100 parts by weight in total of A + B1 + B2 | | | (part(s) by weight) | 20.0 | 20.0 | 20.6 | 12.9 | 29.0 | 17.4 | 34.6 |
| Content of D relative to 100 parts by weight in total of A + B1 + B2 | | | (part(s) by weight) | 3.6 | 2.8 | 3.0 | 2.5 | 2.9 | 2.9 | 3.4 |
| Content of E relative to 100 parts by weight in total of A + B1 + B2 | | | (part(s) by weight) | 18.4 | 19.3 | 22.7 | 13.2 | 13.3 | 29.9 | 35.0 |
| Ca/P ratio | | | | 1.67 | 1.67 | 1.67 | 1.67 | 1.67 | 1.67 | 1.67 |

| | | | | Example 34 | Example 35 | Example 36 | Example 37 | Example 38 | Example 39 |
|---|---|---|---|---|---|---|---|---|---|
| Powder agent | A | Fluoroaluminosilicate glass (D50: 0.5 μm) | (part(s) by weight) | 86.00 | | | | | |
| | | Fluoroaluminosilicate glass (D50: 4 μm) | (part(s) by weight) | | | 86.0 | 86.0 | 86.0 | 86.0 |
| | | Fluoroaluminosilicate glass (D50: 30 μm) | (part(s) by weight) | | 86.0 | | | | |
| | B1 | Tetracalcium phosphate (D50: 5 μm) | (part(s) by weight) | | | | 3.3 | | |
| | | Tetracalcium phosphate (D50: 19 μm) | (part(s) by weight) | 3.3 | 3.3 | | | 3.3 | 3.3 |
| | | Tetracalcium phosphate (D50: 30 μm) | (part(s) by weight) | | | | 3.3 | | |
| | B2 | Anhydrous calcium monohydrogen phosphate (D50: 0.5 μm) | (part(s) by weight) | | | | | 1.2 | |
| | | Anhydrous calcium monohydrogen phosphate (D50: 1 μm) | (part(s) by weight) | 1.2 | 1.2 | 1.2 | 1.2 | | |
| | | Anhydrous calcium monohydrogen phosphate (D50: 5 μm) | (part(s) by weight) | | | | | | 1.2 |
| | | Tricalcium phosphate (D50: 1 μm) | (part(s) by weight) | | | | | | |

TABLE 3-continued

| | | | | | | | | | |
|---|---|---|---|---|---|---|---|---|---|
| | | Anhydrous calcium dihydrogen phosphate (D50: 1 μm) | (part(s) by weight) | | | | | | |
| | — | Hydroxyapatite | (part(s) by weight) | | | | | | |
| | D | L-tartaric acid | (part(s) by weight) | | | | | | |
| | C | Polyalkenic acid powder (acrylic acid/itaconic acid copolymer) | (part(s) by weight) | 9.5 | 9.5 | 9.5 | 9.5 | 9.5 | 9.5 |
| Total | | | (part(s) by weight) | 100.0 | 100.0 | 100.0 | 100.0 | 100.0 | 100.0 |
| Liquid agent | C | Polyalkenic acid (acrylic acid/itaconic acid copolymer) | (part(s) by weight) | 30.1 | 30.1 | 30.1 | 30.1 | 30.1 | 30.1 |
| | D | L-tartaric acid | (part(s) by weight) | 8.9 | 8.9 | 8.9 | 8.9 | 8.9 | 8.9 |
| | E | Water | (part(s) by weight) | 61.0 | 61.0 | 61.0 | 61.0 | 61.0 | 61.0 |
| Total | | | (part(s) by weight) | 100.0 | 100.0 | 100.0 | 1000 | 100.0 | 100.0 |
| Powder-liquid weight ratio | | | | 3.5 | 3.5 | 3.5 | 3.5 | 3.5 | 3.5 |
| Operability | | | | B | B | B | B | A | A |
| Initial compressive strength | | | (MPa) | 201.9 | 200.1 | 201.5 | 194.6 | 199.9 | 199.3 |
| Compressive strength after 30 days | | | (MPa) | 231.4 | 229.9 | 228.9 | 220.3 | 225.3 | 224.5 |
| Increase in compressive strength for 30 days | | | (MPa) | 29.5 | 29.8 | 27.4 | 25.7 | 25.4 | 25.2 |
| Hardness recovery ratio | | | (%) | 41 | 40 | 41 | 38 | 39 | 40 |
| Content of A relative to 100 parts by weight in total of A + B1 + B2 | | | (part(s) by weight) | 95 | 95 | 95 | 95 | 95 | 95 |
| Total content of B1 and B2 relative to 100 parts by weight of in total A + B1 + B2 | | | (part(s) by weight) | 5 | 5 | 5 | 5 | 5 | 5 |
| Content of C relative to 100 parts by weight in total of A + B1 + B2 | | | (part(s) by weight) | 20.0 | 20.0 | 20.0 | 20.0 | 20.0 | 20.0 |
| Content of D relative to 100 parts by weight in total of A + B1 + B2 | | | (part(s) by weight) | 2.8 | 2.8 | 2.8 | 2.8 | 2.8 | 2.8 |
| Content of E relative to 100 parts by weight in total of A + B1 + B2 | | | (part(s) by weight) | 19.3 | 19.3 | 19.3 | 19.3 | 19.3 | 19.3 |
| Ca/P ratio | | | | 1.67 | 1.67 | 1.67 | 1.67 | 1.67 | 1.67 |

TABLE 4

| | | | | Example 40 | Example 41 | Example 42 | Comparative Example 1 | Comparative Example 2 | Comparative Example 3 | Comparative Example 4 |
|---|---|---|---|---|---|---|---|---|---|---|
| Powder agent | A | Fluoroaluminosilicate glass (D50: 0.5 μm) | (part(s) by weight) | | | | | | | |
| | | Fluoroaluminosilicate glass (D50: 4 μm) | (part(s) by weight) | 86.0 | 86.0 | 86.0 | 100.0 | 45.3 | | 95.5 |
| | | Fluoroaluminosilicate glass (D50: 30 μm) | (part(s) by weight) | | | | | | | |
| | BI | Tetracalcium phosphate (D50: 5 μm) | (part(s) by weight) | | | | | | | |
| | | Tetracalcium phosphate (D50: 19 μm) | (part(s) by weight) | 4.2 | 3.2 | 1.0 | | 33.0 | 66.0 | 3.3 |
| | | Tetracalcium phosphate (D50: 30 μm) | (part(s) by weight) | | | | | | | |
| | | Anhydrous calcium monohydrogen phosphate (D50: 0.5 μm) | (part(s) by weight) | | | | | | | |
| | | Anhydrous calcium monohydrogen phosphate (D50: 1 μm) | (part(s) by weight) | 0.3 | 3.5 | | | 12.2 | 24.5 | 1.2 |
| | B2 | Anhydrous calcium monohydrogen phosphate (D50: 5 μm) | (part(s) by weight) | | | | | | | |
| | | Tricalcium phosphate (D50: 1 μm) | (part(s) by weight) | | | | | | | |
| | | Anhydrous calcium dihydrogen phosphate (D50: 1 μm) | (part(s) by weight) | | 1.3 | | | | | |
| | — | Hydroxyapatite | (part(s) by weight) | | | | | | | |
| | D | L-tartaric acid | (part(s) by weight) | | | | | | | |

TABLE 4-continued

| | | | | | | | | | | |
|---|---|---|---|---|---|---|---|---|---|---|
| | C | Polyalkenic acid powder (acrylic acid/itaconic acid copolymer) | (part(s) by weight) | 9.5 | 9.5 | 9.5 | 9.5 | 9.5 | 9.5 | 9.5 |
| Total | | | (part(s) by weight) | 100.0 | 100.0 | 100.0 | 109.50 | 100.00 | 100.00 | 109.50 |
| Liquid agent | C | Polyalkenic acid (acrylic acid/itaconic acid copolymer) | (part(s) by weight) | 30.1 | 30.1 | 30.1 | 30.1 | 30.1 | 30.1 | 30.1 |
| | D | L-tartaric acid | (part(s) by weight) | 8.9 | 8.9 | 8.9 | 8.9 | 8.9 | 8.9 | 0.5 |
| | E | Water | (part(s) by weight) | 61.0 | 61.0 | 61.0 | 61.0 | 61.0 | 61.0 | 69.4 |
| Total | | | (part(s) by weight) | 100.0 | 100.0 | 100.0 | 100.0 | 100.0 | 100.0 | 1000 |
| Powder-liquid weight ratio | | | | 3.5 | 3.5 | 3.5 | 2.3 | 2.3 | 2.3 | 2.3 |
| Operability | | | | A | A | A | A | C | C | D |
| Initial compressive strength | | | (MPa) | 201.1 | 197.3 | 205.1 | 125.4 | 60.7 | 50.2 | 113.1 |
| Compressive strength after 30 days | | | (MPa) | 220.5 | 217.8 | 221.9 | 130.2 | 75.1 | 61.2 | 133.9 |
| Increase in compressive strength for 30 days | | | (MPa) | 19.4 | 20.5 | 16.8 | 4.8 | 14.4 | 11.0 | 20.8 |
| Hardness recovery ratio | | | (%) | 24 | 31 | 23 | 3 | 45 | 49 | 17 |
| Content of A relative to 100 parts by weight in total of A + B1 + B2 | | | (part(s) by weight) | 95 | 95 | 95 | 0 | 0 | 0 | 0 |
| Total content of B1 and B2 relative to 100 parts by weight of in total A + B1 + B2 | | | (part(s) by weight) | 5 | 5 | 5 | 0 | 50 | 100 | 5 |
| Content of C relative to 100 parts by weight in total of A + B1 + B2 | | | (part(s) by weight) | 20.0 | 20.0 | 20.0 | 25.0 | 25.0 | 25.0 | 25.0 |
| Content of D relative to 100 parts by weight in total of A + B1 + B2 | | | (part(s) by weight) | 2.8 | 2.9 | 2.8 | 4.3 | 4.3 | 4.3 | 0.2 |
| Content of E relative to 100 parts by weight in total of A + B1 + B2 | | | (part(s) by weight) | 19.3 | 19.3 | 19.3 | 29.3 | 29.3 | 29.3 | 33.3 |
| Ca/P ratio | | | | 1.90 | 1.40 | 1.20 | — | 1.67 | 1.67 | 1.67 |

| | | | | Comparative Example 5 | Comparative Example 6 | Comparative Example 7 | Comparative Example 8 | Comparative Example 9 | Comparative Example 10 |
|---|---|---|---|---|---|---|---|---|---|
| Powder agent | A | Fluoroaluminosilicate glass (D50: 0.5 μm) | (part(s) by weight) | | | | | | |
| | | Fluoroaluminosilicate glass (D50: 4 μm) | (part(s) by weight) | 95.5 | 95.1 | 71.3 | 86.0 | 86.0 | 83.0 |
| | | Fluoroaluminosilicate glass (D50: 30 μm) | (part(s) by weight) | | | | | | |
| | B1 | Tetracalcium phosphate (D50: 5 μm) | (part(s) by weight) | | | | | | |
| | | Tetracalcium phosphate (D50: 19 μm) | (part(s) by weight) | 3.3 | 3.6 | 2.7 | 3.3 | 3.3 | |
| | | Tetracalcium phosphate (D50: 30 μm) | (part(s) by weight) | | | | | | |
| | | Anhydrous calcium monohydrogen phosphate (D50: 0.5 μm) | (part(s) by weight) | | | | | | |
| | | Anhydrous calcium monohydrogen phosphate (D50: 1 μm) | (part(s) by weight) | 1.2 | 1.3 | 1.0 | 1.2 | 1.2 | |
| | B2 | Anhydrous calcium monohydrogen phosphate (D50: 5 μm) | (part(s) by weight) | | | | | | |
| | | Tricalcium phosphate (D50: 1 μm) | (part(s) by weight) | | | | | | |
| | | Anhydrous calcium dihydrogen phosphate (D50: 1 μm) | (part(s) by weight) | | | | | | |
| | — | Hydroxyapatite | (part(s) by weight) | | | | | | 17.0 |
| | D | L-tartaric acid | (part(s) by weight) | | | | | | |
| | C | Polyalkenic acid powder (acrylic acid/itaconic acid copolymer) | (part(s) by weight) | 9.5 | | 25.0 | 9.5 | 9.5 | 9.5 |
| Total | | | (part(s) by weight) | 109.50 | 100.00 | 100.00 | 100.00 | 100.00 | 109.50 |
| Liquid agent | C | Polyalkenic acid (acrylic acid/itaconic acid copolymer) | (part(s) by weight) | 30.1 | 11.5 | 50.0 | 45.0 | 10.0 | 30.1 |

TABLE 4-continued

| | | | | | | | |
|---|---|---|---|---|---|---|---|
| D | L-tartaric acid | (part(s) by weight) | 25.0 | 8.9 | 8.9 | 15.0 | 2.0 | 8.9 |
| E | Water | (part(s) by weight) | 44.9 | 79.6 | 41.1 | 40.0 | 88.0 | 61.0 |
| Total | | (part(s) by weight) | 100.0 | 100.0 | 100.0 | 100.0 | 100.0 | 100.0 |
| Powder-liquid weight ratio | | | 2.3 | 2.3 | 2.3 | 6.0 | 0.5 | 2.3 |
| Operability | | | B | B | D | D | B | B |
| Initial compressive strength | | (MPa) | not cured | not cured | not cured | unkneadable | not cured | 110.5 |
| Compressive strength after 30 days | | (MPa) | — | — | — | — | — | 115.2 |
| Increase in compressive strength for 30 days | | (MPa) | — | — | — | — | — | 4.7 |
| Hardness recovery ratio | | (%) | — | — | — | — | — | 1 |
| Content of A relative to 100 parts by weight in total of A + B1 + B2 | | (part(s) by weight) | 0 | 0 | 0 | 0 | 0 | 0 |
| Total content of B1 and B2 relative to 100 parts by weight of in total A + B1 + B2 | | (part(s) by weight) | 5 | 5 | 5 | 5 | 5 | — |
| Content of C relative to 100 parts by weight in total of A + B1 + B2 | | (part(s) by weight) | 25.0 | 5.0 | 47.8 | 18.8 | 32.5 | 25.0 |
| Content of D relative to 100 parts by weight in total of A + B1 + B2 | | (part(s) by weight) | 12.0 | 3.9 | 5.2 | 2.8 | 4.4 | 4.3 |
| Content of E relative to 100 parts by weight in total of A + B1 + B2 | | (part(s) by weight) | 21.6 | 34.6 | 23.8 | 7.3 | 194.0 | 29.3 |
| Ca/P ratio | | | 1.67 | 1.67 | 1.67 | 1.67 | 1.67 | — |

The invention claimed is:

1. A dental curable composition comprising:
fluoroaluminosilicate glass particles (A), basic calcium phosphate particles (B1), acidic calcium phosphate particles (B2), a polyalkenic acid (C), tartaric acid (D), and water (E), wherein the tartaric acid (D) is L-tartaric acid,
wherein
the dental curable composition comprises from 70 to 99 parts by weight of the fluoroaluminosilicate glass particles (A), from 1 to 30 parts by weight in total of the basic calcium phosphate particles (B1) and the acidic calcium phosphate particles (B2), from 10 to 40 parts by weight of the polyalkenic acid (C), from 0.3 to 10 parts by weight of the tartaric acid (D), and from 10 to 90 parts by weight of the water (E) each relative to 100 parts by weight in total of the fluoroaluminosilicate glass particles (A), the basic calcium phosphate particles (B1), and the acidic calcium phosphate particles (B2), and a Ca/P ratio of a sum of the basic calcium phosphate particles (B1) and the acidic calcium phosphate particles (B2) is from 1.10 to 1.95.

2. The dental curable composition according to claim 1, wherein the basic calcium phosphate particles (B1) are at least one member selected from the group consisting of particles of tetracalcium phosphate [$Ca_4(PO_4)_2O$] and particles of octacalcium phosphate pentahydrate [$Ca_8H_2(PO_4)_6 \cdot 5H_2O$], and the acidic calcium phosphate particles (B2) are at least one member selected from the group consisting of particles of anhydrous calcium monohydrogen phosphate [$CaHPO_4$], particles of tricalcium phosphate [$Ca_3(PO_4)_2$], particles of anhydrous calcium dihydrogen phosphate [$Ca(H_2PO_4)_2$], particles of amorphous calcium phosphate [$Ca_3(PO_4)_2 \cdot xH_2O$], particles of acidic calcium pyrophosphate [$CaH_2P_2O_7$], particles of calcium monohydrogen phosphate dihydrate [$CaHPO_4 \cdot 2H_2O$], and particles of calcium dihydrogen phosphate monohydrate [$Ca(H_2PO_4)_2 \cdot H_2O$].

3. The dental curable composition according to claim 1, wherein the dental curable composition is a glass ionomer cement.

4. A method for producing a dental curable composition according to claim 1, the method comprising mixing a powder agent (X) comprising at least fluoroaluminosilicate glass particles (A), basic calcium phosphate particles (B1), and acidic calcium phosphate particles (B2), with a liquid agent (Y) comprising at least a polyalkenic acid (C), tartaric acid (D), and water (E), wherein
a weight ratio (X/Y) of the powder agent (X) to the liquid agent (Y) is from 1.0 to 5.0.

5. The method for producing a dental curable composition according to claim 4, wherein the fluoroaluminosilicate glass particles (A) have an average particle size of from 0.3 to 35 μm, the basic calcium phosphate particles (B1) have an average particle size of from 3 to 35 μm, and the acidic calcium phosphate particles (B2) have an average particle size of from 0.3 to 10 μm.

6. A dental curable composition kit comprising:
a powder agent (X) comprising at least fluoroaluminosilicate glass particles (A), basic calcium phosphate particles (B1), and acidic calcium phosphate particles (B2), and
a liquid agent (Y) comprising at least a polyalkenic acid (C), tartaric acid (D), and water (E), wherein the tartaric acid (D) is L-tartaric acid, and
wherein the powder agent (X) and the liquid agent (Y) are mixed in a weight ratio (X/Y) within a range of from 1.0 to 5.0.

7. The dental curable composition kit according to claim 6, wherein the fluoroaluminosilicate glass particles (A) have an average particle size of from 0.3 to 35 μm, the basic calcium phosphate particles (B1) have an average particle size of from 3 to 35 μm, and the acidic calcium phosphate particles (B2) have an average particle size of from 0.3 to 10 μm.

8. The dental curable composition according to claim 1, comprising from 0.3 to 7 parts by weight of the tartaric acid (D).

9. The dental curable composition according to claim 1, comprising from 0.3 to 5 parts by weight of the tartaric acid (D).

10. The method for producing a dental curable composition according to claim 1, wherein the fluoroaluminosilicate glass particles (A) have an average particle size of from 0.5 to 30 μm.

11. The method for producing a dental curable composition according to claim 1, comprising from 2 to 20 parts by weight in total of the basic calcium phosphate particles (B1) and the acidic calcium phosphate particles (B2).

12. The method for producing a dental curable composition according to claim 1, comprising from 3 to 10 parts by weight in total of the basic calcium phosphate particles (B1) and the acidic calcium phosphate particles (B2).

13. The method for producing a dental curable composition according to claim 1, wherein the basic calcium phosphate particles (B1) have an average particle size of from 5 to 30 µm.

14. The method for producing a dental curable composition according to claim 1, wherein the basic calcium phosphate particles (B1) have an average particle size of from 5 to 30 µm.

15. The method for producing a dental curable composition according to claim 1, wherein the acidic calcium phosphate particles (B2) have an average particle size of from 0.5 to 5 µm.

16. The method for producing a dental curable composition according to claim 1, wherein the Ca/P ratio of a sum of the basic calcium phosphate particles (B1) and the acidic calcium phosphate particles (B2) is from 1.1 to 1.7.

17. The method for producing a dental curable composition according to claim 1, comprising from 10 to 30 parts by weight of the polyalkenic acid (C).

18. The method for producing a dental curable composition according to claim 1, wherein the polyalkenic acid (C) is at least one polymer selected from the group consisting of a homopolymer and copolymer of acrylic acid, methacrylic acid, 2-chloroacrylic acid, 2-cyanoacrylic acid, aconitic acid, mesaconic acid, maleic acid, itaconic acid, fumaric acid, glutaconic acid, citraconic acid, and utraconic acid.

19. The method for producing a dental curable composition according to claim 1, wherein the polyalkenic acid (C) is a polymer having a weight average molecular weight of from 5,000 to 50,000 and contains no polymerizable ethylenically unsaturated double bonds.

20. The method for producing a dental curable composition according to claim 1, further comprising at least component selected from the group consisting of a filler and a pigment.

* * * * *